(12) United States Patent
Yang

(10) Patent No.: US 8,865,003 B2
(45) Date of Patent: Oct. 21, 2014

(54) APPARATUS AND METHOD FOR SEPARATION OF PARTICLES SUSPENDED IN A LIQUID FROM THE LIQUID IN WHICH THEY ARE SUSPENDED

(75) Inventor: Tahua Yang, Woodridge, IL (US)

(73) Assignee: Abbott Laboratories, Abbott Park, IL (US)

( * ) Notice: Subject to any disclaimer, the term of this patent is extended or adjusted under 35 U.S.C. 154(b) by 1099 days.

(21) Appl. No.: 12/238,544

(22) Filed: Sep. 26, 2008

(65) Prior Publication Data

US 2010/0078384 A1    Apr. 1, 2010

(51) Int. Cl.
*B01D 17/06*    (2006.01)
*B01L 3/00*    (2006.01)
*A61M 1/36*    (2006.01)
*B01D 21/28*    (2006.01)
*G01N 33/49*    (2006.01)

(52) U.S. Cl.
CPC ....... *B01D 21/283* (2013.01); *B01L 2400/0439* (2013.01); *B01L 3/502776* (2013.01); *B01L 2200/0647* (2013.01); *A61M 1/3678* (2014.02); *G01N 33/491* (2013.01)
USPC . 210/748.05; 210/243; 210/645; 210/748.01; 210/153; 210/738; 250/281; 250/288; 250/493.1; 422/20; 422/44; 422/128; 310/311; 310/313 R; 310/322

(58) Field of Classification Search
USPC .......... 210/748.02, 748.05, 748.01, 767, 348, 210/339, 383, 384, 738; 422/20, 128, 44; 310/311, 313 R, 313, 322, 323.19, 19; 250/281, 288, 493.1
See application file for complete search history.

(56) References Cited

U.S. PATENT DOCUMENTS 3,832,655 A * 8/1974 Yokoyama .................... 333/142
4,055,491 A   10/1977 Porath-Furedi
(Continued)

FOREIGN PATENT DOCUMENTS

EP    380194 A1    8/1990
JP    9122480       5/1997
(Continued)

OTHER PUBLICATIONS

Groschl, M., Ultrasonic Separation of Suspended Particles—Part I: Fundamentals, Acustica, vol. 84, (1998) 432-447.
(Continued)

*Primary Examiner* — Joseph Drodge
*Assistant Examiner* — Cameron J Allen
(74) *Attorney, Agent, or Firm* — Hanley, Flight & Zimmerman, LLC

(57) ABSTRACT

A method for separating, or removing, particulate material, e.g., blood cells, from a sample of fluid, e.g., whole blood of a patient, in which the particulate material is suspended. In the case of separating blood cells from blood plasma or blood serum, the resulting samples of blood plasma or blood serum can be used for in vitro diagnostic applications. In normal practice, a whole blood sample of a patient are provided and then introduced into an apparatus that contains a flow channel. An acoustic field, which contains acoustic standing waves from external ultrasonic transducers, is located within the flow channel. Laminar flow is maintained in the flow channel. Blood cells and platelets are separated from blood plasma or blood serum at the end of the flow channel and collected. The method described herein allows fluid components to differentially migrate to areas of preferred acoustic interaction. The parameters that affect separation of particles are size, density, compressibility of the particles, and the fluid surrounding the particles.

35 Claims, 21 Drawing Sheets

(56) References Cited

U.S. PATENT DOCUMENTS

| | | | |
|---|---|---|---|
| 4,673,512 A | 6/1987 | Schram | |
| 4,983,189 A | 1/1991 | Peterson et al. | |
| 4,998,553 A | 3/1991 | Schram | |
| 5,186,844 A | 2/1993 | Burd et al. | |
| 5,225,089 A | 7/1993 | Benes et al. | |
| 5,711,888 A | 1/1998 | Trampler et al. | |
| 5,902,489 A | 5/1999 | Yasuda et al. | |
| 6,297,061 B1 | 10/2001 | Wu et al. | |
| 6,881,314 B1 | 4/2005 | Wang et al. | |
| 2002/0127144 A1* | 9/2002 | Mehta | 422/81 |
| 2004/0069717 A1* | 4/2004 | Laurell et al. | 210/748 |
| 2004/0146954 A1* | 7/2004 | Waldman et al. | 435/7.23 |
| 2004/0217069 A1* | 11/2004 | Columbus | 210/782 |
| 2006/0021437 A1 | 2/2006 | Kaduchak et al. | |
| 2006/0037915 A1* | 2/2006 | Strand et al. | 210/748 |
| 2006/0037916 A1* | 2/2006 | Trampler | 210/748 |
| 2008/0290037 A1 | 11/2008 | Liu | |
| 2009/0014360 A1 | 1/2009 | Toner et al. | |
| 2009/0029870 A1 | 1/2009 | Ward et al. | |
| 2009/0048805 A1 | 2/2009 | Kaduchak et al. | |
| 2009/0053106 A1 | 2/2009 | Wu et al. | |
| 2009/0107909 A1 | 4/2009 | Kotera et al. | |
| 2009/0147253 A1 | 6/2009 | Hartmann et al. | |
| 2009/0158823 A1 | 6/2009 | Kaduchak et al. | |
| 2009/0162887 A1* | 6/2009 | Kaduchak et al. | 435/29 |
| 2009/0188795 A1 | 7/2009 | Oakey et al. | |

FOREIGN PATENT DOCUMENTS

| | | |
|---|---|---|
| JP | 11262880 | 9/1999 |
| JP | 3021340 | 3/2000 |
| JP | 2001525722 | 12/2001 |
| JP | 2007285908 | 11/2007 |
| JP | 2008173569 | 7/2008 |
| WO | WO-9005008 A1 | 5/1990 |
| WO | 98/50133 | 11/1998 |
| WO | 2004033087 | 4/2004 |
| WO | 2006032703 A1 | 3/2006 |
| WO | 2009086043 A2 | 7/2009 |
| WO | 2009123555 A1 | 10/2009 |

OTHER PUBLICATIONS

Invitation to Pay Additional Fees and, Where Applicable, Protest Fees, PCT/US2009/057940, mailed on Feb 8, 2010, 8 pages.

Japanese Patent Office, "Office Action," issued in connection with corresponding application No. JP 2011-529167, mailed on Jul. 16, 2013, 8 pages.

Arbitrary Function Generators [online], [retrieved on Sep. 18, 2008]. Retrieved from the Internet: <URL: http://www.ndt-ed.org/EducationResources/CommunityCollege/Ultrasonics/EquipmentTrans/functiongenerators.htm>, pp. 1-2.

Agilent 33120A, Function/Arbitrary Waveform Generator Data Sheet, 2001, 2004, pp. 1-4, Agilent Technologies, Inc., U.S.A.

Model PA-4 RF Power Amplifier. Datasheet [online] IntraAction Corp., 2008 [retrieved on Sep. 17, 2008]. Retrieved from the Internet: <URL: http://www.intraaction.com>, pp. 1-3.

Bulk micromachining—Wikipedia the free encyclopedia [online], [retrieved on Sep. 11, 2008]. Retrieved from the Internet: <URL: http://en.wikipedia.org/wiki/Bulk_micromachining>, p. 1.

Deep reactive-ion etching—Wikipedia the free encyclopedia [online], [retrieved on Sep. 11, 2009]. Retrieved from the Internet: <URL: http://en.wikipedia.org/wiki/DRIE>, pp. 1-2.

Etching (microfabrication)—Wikipedia the free encyclopedia [online], [retrieved on Sep. 11, 2008]. Retrieved from the Internet: <URL: http://en.wikipedia.org/wiki/Etching_(microfabrication)>, pp. 1-5.

Function generator—Wikipedia the free encyclopedia [online], [retrieved on Sep. 11, 2008]. Retrieved from the Internet: <URL: http://en.wikipedia.org/wiki/Function_generator>, pp. 1-2.

Gaida, et al., Selective Retention of Viable Cells in Ultrasonic Resonance Field Devices, Biotechnol. Prog., 1996, vol. 12, No. 1, pp. 73-76.

Kapishnikov, et al., Continuous particle size separation and size sorting using ultrasound in a microchannel, J. Stat. Mech. 2006, P01012, pp. 1-15.

Knights, Micro Molds Make Micro Parts, Plastics Technology [online], [retrieved on Sep. 11, 2008]. Retrieved from the Internet: <URL: http://www.ptonline.com/articles/200212fal.html>, pp. 1-5.

Lach, et al., Piezoelectric materials for ultrasonic probes [online], [retrieved on Apr. 22, 2008]. Retrieved from the Internet: <URL: http://www.ndt.net/article/platte2/platte2.htm>, pp. 1-8.

Olympus. Panametrics-NDT™ Ultrasonic Transducers, pp. 1-49, 920-041C-EN, Olympus NDT™, 2006.

Photoresist—Wikipedia the free encyclopedia [online], [retrieved on Sep. 11, 2008]. Retrieved from the Internet: <URL: http://en.wikipedia.org/wiki/Negative_resist>, pp. 1-4.

Piezoelectric Transducers. NDT Resource Center [online], [retrieved on Sep. 18, 2008]. Retrieved from the Internet: <URL: http://www.ndt-ed.org/EducationResources/CommunityCollege/Ultrasonics/EquipmentTrans/piezotransducers.htm, pp. 1-2.

Pui, et al., Batch and Semicontinuous Aggregation and Sedimentation of Hybridoma Cells by Acoustic Resonance Fields, Biotechnol. Prog. 1995, 11, pp. 146-152.

Signal generator—Wikipedia the free encyclopedia [online], [retrieved on Aug. 20, 2008]. Retrieved from the Internet: <URL: http://en.wikipedia.org/wiki/Signal_generator>, pp. 1-2.

Soft lithography—Wikipedia the free encyclopedia [online], [retrieved on Sep. 11, 2008]. Retrieved from the Internet: <URL: http://en.wikipedia.org/wiki/Soft_lithography>, pp. 1-2.

Stanford Research Systems PS310 12—1250 V, 0.02 AMP, DC High Voltage Power Supply. Datasheet [online]. Stanford Research Systems [retrieved on Sep. 11, 2008]. Retrieved from the Internet: <URL: http://www.valuetronics.com/Details.aspx?Model=Stanford%20Research%20Systems_PS310&ProdID=1240>, pp. 1-2.

Standing wave—Wikipedia the free encyclopedia [online], [retrieved on Sep. 17, 2008]. Retrieved from the Internet: <URL: http://en.wikipedia.org/wiki/Standing_wave>, pp. 1-4.Standing_wave>, pp. 1-4.

SU-8 photoresist—Wikipedia the free encyclopedia [online], [retrieved on Sep. 11, 2008]. Retrieved from the Internet: <URL: http://en.wikipedia.org/wiki/SU-8_photoresist>, p. 1.

Transducer Types. NDT Resource Center [online], [retrieved on Sep. 18, 2008]. Retrieved from the Internet: <URL: http://www.ndt-ed.org/EducationResources/CommunityCollege/Ultrasonics/EquipmentTrans/transducertypes.htm, pp. 1-3.

Yosioka, et al., Acoustic Radiation Pressure on a Compressible Sphere, Acustica, vol. 5, 1955, pp. 167-173.

International Search Report, issued by the International Searching Authority in connection with corresponding International patent application No. PCT/US2009/057940, mailed on Jul. 21, 2010, 7 pages.

International Preliminary Report on Patentability and Written Opinion, issued by the International Searching Authority in connection with corresponding International patent application No. PCT/US2009/057940, mailed on Mar. 29, 2011, 11 pages.

Examiner's Decision of Rejection, issued by the Japanese Intellectual Property Office in connection with Japanese Patent Application No. 2011-529167, mailed on Apr. 28, 2014, 5 pages.

* cited by examiner

APPARATUS AND METHOD FOR SEPARATION OF PARTICLES SUSPENDED IN A LIQUID FROM THE LIQUID IN WHICH THEY ARE SUSPENDED

BACKGROUND OF THE INVENTION

1. Field of the Invention

This invention relates to the separation of particles from a liquid in which the particles are suspended, more particularly, the separation of blood cells from the blood plasma or the blood serum in which they are suspended.

2. Discussion of the Art

For in vitro diagnostics, biological samples currently used are samples of blood plasma or samples of blood serum. Disease markers related to proteins, lipoproteins, hormones, antibodies, antigens, virus, bacteria, parasites are commonly detected in blood plasma or blood serum of a patient. In order to collect blood plasma or blood serum, red blood cells, white blood cells, platelets, and other components must be removed from a sample of whole blood. Blood plasma makes up about 55% of total blood volume. It is composed mostly of water (90% by volume) and contains dissolved proteins, glucose, clotting factors, mineral ions, hormones, and carbon dioxide (plasma being the main medium for excretory product transportation). Blood serum is blood plasma without fibrinogen or the other clotting factors. Blood cells must be removed from blood plasma or blood serum before the sample of blood can be analyzed.

Centrifugation and filtration are currently used to separate blood cells from blood plasma or blood serum for diagnostic purposes. Both techniques require extensive labor and a relatively great amount of time for medical laboratories, which have limited resources with respect to both equipment and personnel. The drawbacks of centrifugation, wherein whole blood samples are introduced into a centrifuge rotating at 3000-3400 rpm for 10 to 15 minutes, include consumption of time, which results from the time needed by a technician to load and unload samples, the need for a skilled technician to aspirate blood plasma or blood serum with a pipette from the separated layers in blood collection tubes. The drawbacks of filtration processes include filter fouling and low throughput after fouling occurs. Other potential problems include breakage of blood collection tubes and loss of the sample. There is also the risk of hemolysis and the consequent destruction of the sample. Accordingly, it would be desirable to provide a method that is cost effective and efficient for the separation of blood cells from blood plasma or blood serum in order to analyze a sample of blood.

U.S. Patent Application Publication No. 2006/0021437 A1 discloses an apparatus and a method for concentrating analytes within a fluid flowing through a tube using acoustic radiation pressure. The apparatus includes a function generator that outputs a radio frequency electrical signal to a transducer that transforms the radio frequency electric signal to an acoustic signal and couples the acoustic signal to the tube. The acoustic signal is converted within the tube to acoustic pressure that concentrates the analytes within the fluid.

U.S. Pat. No. 5,711,888 discloses separation and recycling of particulate material suspended in a fluid by means of an ultrasonic resonance wave. In a preferred embodiment, the ultrasonic resonance field is generated within a multilayered composite resonator system including a transducer, the suspension, and a mirror parallel to each other. Dimensions and frequencies resonant to the whole system but not exciting Eigen-frequencies of transducer and mirror itself are chosen so that thermal dissipation is minimized. Specialized applications in biotechnology are described including an acoustic filter for mammalian cell bioreactors or the selective retention of viable cells relative to nonviable cells.

WO 2006/032703 A1 discloses a method and a device for separating particles using ultrasonic standing waves which are switched between two different frequencies. A second order harmonic standing wave is used together with a fundamental standing wave. If the particles are exposed to the fundamental standing wave, the forces act to collect particles at the center. If the particles are exposed to the second order harmonic standing wave, the forces act to collect particles at the two pressure nodes at the sides. By switching the frequency between the second order harmonic standing wave and the fundamental standing wave, particles with different properties will be exposed to different accelerations and are separated into two streams.

U.S. Pat. No. 3,832,655 discloses an ultrasonic delay line which comprises a solid body and two input and output electro-mechanical transducers for converting electrical energy into ultrasonic mechanical energy or vice versa, and in which the ultrasonic wave, emitted from the input electro-mechanical transducer by the application of an electrical input signal thereto, is reflected by at least one reflecting surface formed in the solid body and enters the output electro-mechanical transducer to derive therefrom an electric output signal which is delayed behind the electric input signal for a period of time during which the ultrasonic wave propagates in the solid body. The reflecting surface has at least one elliptical surface whose focuses are located each at one point on each electro-mechanical transducer or its equivalent point.

U.S. Pat. No. 4,055,491 discloses apparatus and method for using ultrasonic waves for removing microscopic particles from a liquid medium, such as algae from a solar or refuse pond, or blood cells from blood. The apparatus includes an ultrasonic generator propagating ultrasonic waves of over one megacycle per second through the liquid medium to cause the flocculation of the microscopic particles at spaced points. In two embodiments, the ultrasonic waves are propagated in the horizontal direction through the liquid medium, and baffle plates are disposed below the level of propagation of the ultrasonic waves. The baffles are oriented to provide a high resistance to the horizontal propagation therethrough of the ultrasonic waves and a low-resistance to the vertical settling therethrough of the flocculated particles. The ultrasonic generator is periodically energized to flocculate the particles, and then de-energized to permit the settling of the flocculated particles through the baffle plates from whence they are removed.

U.S. Pat. No. 4,673,512 discloses the separation of different types of particulate matter in a carrier liquid by using ultrasonic standing wave and relying on the different acoustic responses of the different particle types. By varying the acoustic energy propagation cyclically a more effective separation rate can be obtained, with a more readily attracted particle type being subjected to a further discrimination step in each cycle. The cyclical energy variation may be in the intensity of the standing wave, e.g., using suppression means, and/or the velocity of the standing wave relative to the liquid medium, e.g., using phase control means.

Pui et al., Batch and Semicontinuous Aggregation and Sedimentation of Hybridoma Cells by Acoustic Resonance Fields, *Biotechnol. Prog.* 1995, 11, 146-152, discloses the use of ultrasound to enhance the sedimentation of hybridoma cells from medium in a 75 mL resonator chamber. Forces in the acoustic standing waves aggregated the cells, and the aggregates were then rapidly sedimented by gravity. Cell separation increased with acoustic treatment time and cell concentration.

Gaida et al., Selective Retention of Viable Cells in Ultrasonic Resonance Field Devices. *Biotechnol. Prog.* 1996, 12, 73-76, discloses a double chamber ultrasonic resonance field device for the separation and retention of animal cells. By controlling operational parameters such as flow and power input, the device can retain viable cells more efficiently, allowing for selective removal of nonviable cells and cell debris.

Other techniques for separating blood cells from blood plasma or blood serum include electro-osmotic flow, which involves separation by size differential, which requires a conductive medium in a strong electric field, centrifugal force, as described in U.S. Pat. No. 5,186,844, magnetic separation, which requires the generation of a magnetic field either by high current or mechanical movement of magnets, dielectrophoretic separation, which requires high voltages with a non-conductive medium, as described in U.S. Pat. No. 6,881,314, electrophoretic separation, which requires high voltages with a conductive medium, such as electrolytes, as described in U.S. Pat. No. 6,881,314, diffusion-based separation, as described in U.S. Pat. No. 6,297,061, and optical trapping, which requires a single beam infrared laser, as described in U.S. Pat. No. 4,893,886.

Acoustic radiation forces can be expressed by the following equation:

$$F_{st} = \frac{2\pi(\kappa R)^3 2E_{st}}{\kappa^2}\Phi(\Lambda, \sigma)\sin(2\kappa r_0)$$

$$\Phi(\Lambda, \sigma) = \frac{1}{3}\left(\frac{5\Lambda - 2}{2\Lambda + 1} - \frac{1}{\Lambda\sigma^2}\right)$$

where
$F_S$, represents the primary acoustic force acting on a particle;
$E_{st}$ represents the energy density of standing waves;
$\Lambda$ represents the ratio of the density of the particle to the density of the fluid;
$\sigma$ represents the ratio of the velocity of sound of the particle to the velocity of sound of the fluid;
R represents the radius of the particle;
$r_o$ represents the vector normal to the force node; and
k represents the sound wavenumber (sound frequency).
See, for example, Kapishnikov et al., Continuous particle size separation and size sorting using ultrasound in a microchannel, Journal of Statistical Mechanics: Theory and Experiment, IOP Publishing, 2006, pages 1-15, incorporated herein by reference. The acoustic radiation force on a particle is influenced by the size, density, compressibility, and location of the particle, and the frequency and amplitude of acoustic radiation.

SUMMARY OF THE INVENTION

In one aspect, this invention provides a method for separating, or removing, blood cells from a sample of whole blood of a patient. The resulting samples of blood plasma or blood serum can be used for in vitro diagnostic applications. In normal practice, a whole blood sample of a patient is provided and then introduced into an apparatus that contains a flow channel. An acoustic field, which contains acoustic standing waves generated by external ultrasonic transducers, is located within the flow channel. Laminar flow is maintained in the flow channel. Blood cells are separated from blood plasma or blood serum at the end of the flow channel and collected.

Acoustic standing waves generated by ultrasonic transducers provide a means for manipulating suspended particles in a fluid without contacting the suspended particles. The acoustic standing waves maintain acoustic nodes and antinodes in different layers of the path of the flow of fluid. The method described herein allows components of the fluid to differentially migrate to areas of preferred acoustic interaction. The parameters that affect the separation of blood cells from blood plasma or blood serum are size, density, and compressibility of red blood cells, white blood cells, and platelets, and the fluid surrounding the red blood cells, white blood cells, and platelets.

In one embodiment, a batch process is employed to effect separation of blood cells from blood plasma or blood serum in a test tube or plurality of test tubes. An acoustic energy transducer is coupled with a delay line. The acoustic node of the standing wave is placed at a location near the bottom of the test tube. The primary force acting upon the moving blood cells is acoustic, and the secondary force acting upon the blood cells is gravitational. The air serves as a reflective medium at the interface of blood and air, because of the large differences of the acoustic impedances between air and blood. After the acoustic separation process, blood cells are concentrated in the bottom layer of the test tube and blood plasma or blood serum is presented in the upper layer. The upper layer can then be removed by manual aspiration, as by means of a pipette, or robotic aspiration, as by means of a robotic pipette, for subsequent processes.

In another embodiment, a continuous process is employed to effect separation of blood cells from blood plasma or blood serum in a flow channel. The flow channel is constructed with dimensions that allow the flow of the sample to be laminar. A plurality of parallel or substantially parallel layers is preferred for maintaining laminar flow in the flow channel. However, the layers forming the flow channel need not be parallel so long as laminar flow of the fluid is maintained in the flow channel. A plurality of ultrasonic transducers with coupling delay lines can be attached to the layers that form the walls of the flow channel. It is preferred that the ultrasonic transducers be arranged so that the incident angle of the acoustic wave to the wall of the flow channel is approximately 45°. The coupling delay lines provide a means for removing the near field acoustic effect, which is unstable. Utilizing refraction and reflection of sound waves and standing waves with nodes facilitates the concentration of blood cells and platelets at the center of the flow channel. When whole blood flows through the flow channel, blood cells are concentrated in a central zone by acoustic energy. At a collection zone of the flow channel, the gap of the flow channel can be expanded gradually to maintain laminar in the flow path and to avoid turbulence. The expanded gap in the collection zone of the flow channel facilitates collection of blood cells and collection of blood plasma or blood serum.

The method described herein can be used for pre-analytics, flow cytometry, and separation of cells based on size differences. Pre-analytics involves the preparation of samples or specimens of a patient to provide blood plasma or blood serum. The processed samples or specimens of blood plasma or blood serum can be used to perform in vitro diagnostic analysis, such as, for example, immunoassays, clinical chemistry assays. Because the acoustic separation technique described herein allows cells to be positioned at selected locations of a flow channel, the technique can be coupled with flow cytometry to align cells along light paths. The acoustic forces exerted on different cells depend on several factors, such as, for example, size, density, position, compressibility of red blood cells, white blood cells, and platelets, and the fluid surrounding the red blood cells, white blood cells, and platelets. Accordingly, the separation of blood cells and platelets based on physical size is possible.

BRIEF DESCRIPTION OF THE DRAWINGS

In FIG. 2A, the acoustic radiation force has not been applied. In FIG. 2B, the acoustic radiation force has been applied.

In FIG. 10A, the ultrasonic transducers are custom-designed ultrasonic transducers.

In FIG. 10B, the ultrasonic transducers are commercially available ultrasonic transducers.

FIG. 11A shows acoustic standing waves that have been generated by the ultrasonic transducers shown in FIG. 10A.

FIG. 11B shows acoustic standing waves that have been generated by the ultrasonic transducers shown in FIG. 10B.

FIG. 11C shows particles flowing parallel to the walls of the flow channel.

FIG. 11D shows particles flowing parallel to the walls of the flow channel.

In FIG. 12, the ultrasonic transducers are not shown. The fluid in the flow channel is represented by parallel, hatched lines.

In FIG. 13, the ultrasonic transducers are not shown. The fluid in the flow channel is represented by parallel, hatched lines.

In FIG. 14, the ultrasonic transducers are not shown. The fluid in the flow channel is represented by parallel, hatched lines.

In FIG. 15, the ultrasonic transducers are not shown. The fluid in the flow channel is represented by parallel, hatched lines. In the embodiment shown in FIG. 15, the width of the flow channel increases between (a) the inlet channel and (b) the first and second outlet channels and decreases between (a) the first and second outlet channels and (b) third outlet channel.

DETAILED DESCRIPTION

As used herein, the expression "acoustic energy" refers to focused continuous and pulse acoustic energy with frequency typically higher that 20 KHz and less than 100 MHz. The wavelength corresponding to 20 KHz is about 7 cm and 100 MHz is about 14.5 micrometers in aqueous medium.

As used herein, the expressions "standing wave", "stationary wave", and the like mean a non-propagating wave that is generated by the interference of two waves moving in opposite directions. The frequencies of two waves must be the same to produce standing waves. Standing waves have nodes and anti-nodes. At nodes, the displacement is zero, and at antinodes the displacement is maximum. See, for example, the discussion of standing wave at the web site http://en.wikipedia.org/wiki/Standing_wave.

Figure 1:
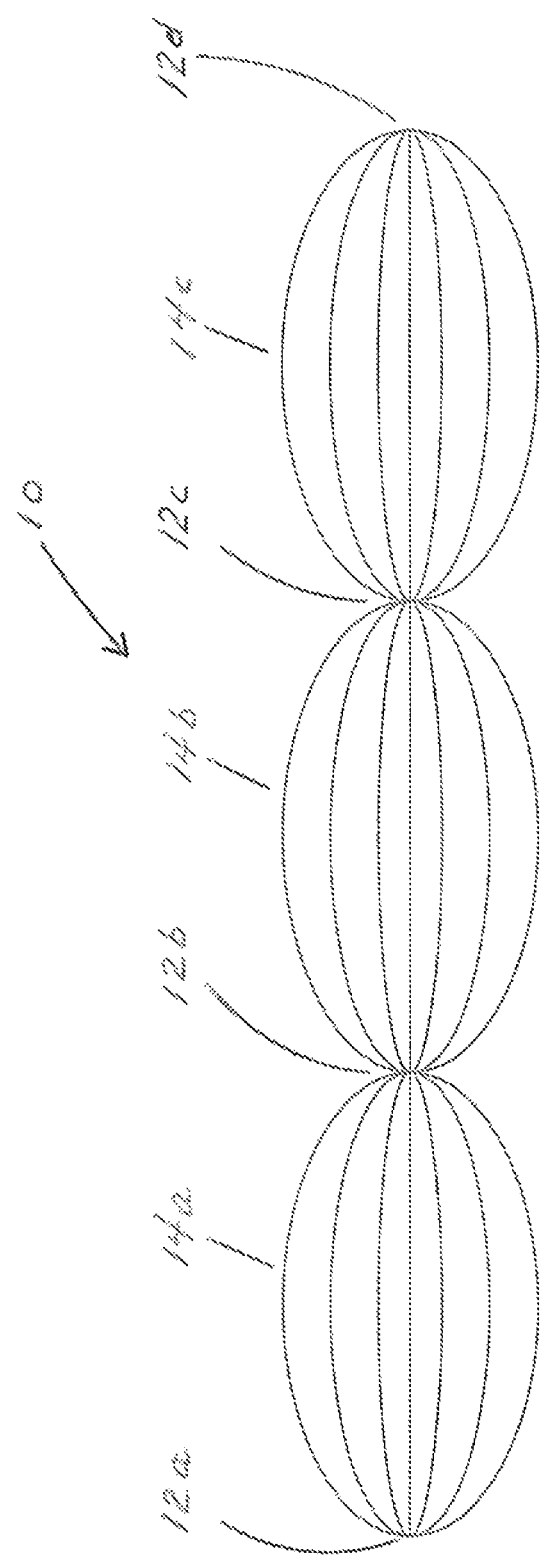
FIG. 1 is a schematic diagram illustrating acoustic standing waves with nodes and antinodes.
Figure 2B:
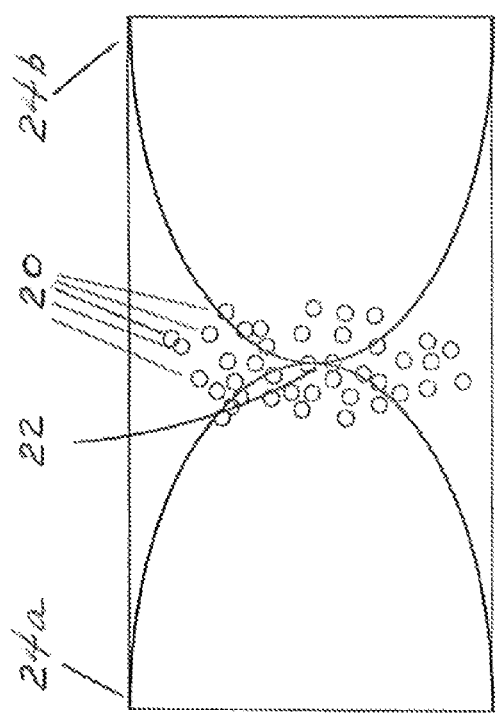
FIGS. 2A and 2B are schematic diagrams illustrating separation of particles from liquid on account of acoustic radiation forces.
Figure 2A:
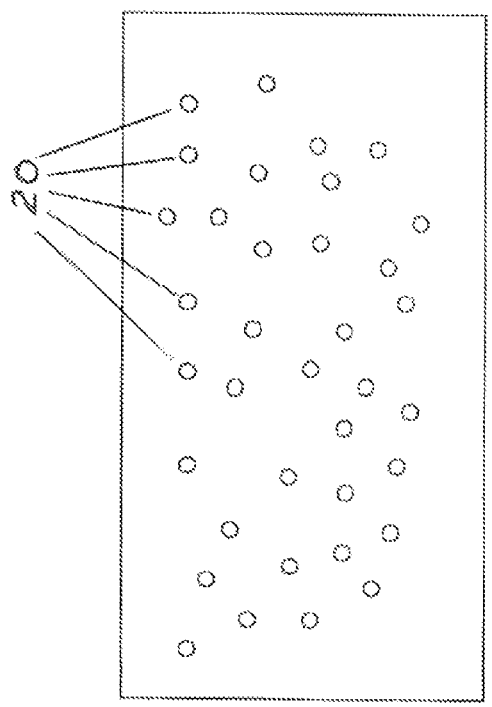

As used herein, the term "node" means the places where the medium does not move. As used herein, the term "antinode" means the places where the medium experiences maximal vibration. FIG. 1 shows an acoustic standing wave 10 having nodes 12a, 12b, 12c, and 12d, and anti-nodes 14a, 14b, and 14c. FIGS. 2A and 2B show separation of particles by means of acoustic radiation forces. In FIG. 2A, the particles 20 have not been separated. In FIG. 2B, the particles 20 have been concentrated at the node 22 and antinodes 24a, 24b. Acoustic radiation forces urge the particles toward the node 22, in accordance with the acoustic radiation force equation set forth previously.

As used herein, the expressions "ultrasonic transducer", "acoustic energy transducer" mean a device that converts electrical energy to mechanical energy, in the form of sound, and vice versa. Ultrasonic transducers are further described in Panametrics-NDT™ Ultrasonic Transducers Brochure 920-041C-EN, 2008, Olympus NDT, Waltham, Mass., pages 1-49, incorporated herein by reference.

As used herein, the expression "delay line transducer" means a single element longitudinal wave transducer used in conjunction with a replaceable delay line. The primary function of a delay line transducer is to introduce a time delay between the generation of the sound wave and the arrival of any reflected waves, thereby allowing the transducer to complete its "sending" function before it starts its "listening" function so that near surface resolution is improved. The delay allows the element of the transducer to stop vibrating before a return signal from a reflector can be received. The acoustic field generated by a transducer can be divided by two zones. The zones are characterized on the basis of their distance from the face of the transducer. The near field is the zone closer to the transducer, and the near field exhibits significant variations. The far field is defined as a zone starting with the end of the near field distal from the transducer, and the far field is stable and predictable. The delay line allows only the stable far field to be used. The key feature of the delay line is that the material selected needs to be transparent to the sound field, or to be minimally reflective of sound.

As used herein, the expression "acoustic impedance" means product of the density of a material and acoustic velocity. At the interface of two different materials, the difference in acoustic impedances determines acoustic transmission and reflection at the interface.

As used herein, the expression "SU-8 photoresist" means a negative photoresist. It is a very viscous polymer that can be spun or spread over a thickness ranging from one micrometer up to two millimeters and still be processed with standard mask aligner. SU-8 is mainly used for fabrication of devices for microfluidics.

As used herein, the expressions "micro mold", "micro molding", and the like, refer to tooling and the use thereof for producing millimeter-sized and micrometer-sized parts for various fields, such as, for example, biomedical, pharmaceutical, electronics, microfluidics. See, for example, Micro Molds Make Micro Parts, Plastics Technology, December 2002, http://www.pyonline.com/articles/200212fa1.html, incorporated herein by reference.

As used herein, the expression "soft lithography" refers to a family of techniques for fabricating or replicating structures using "elastomeric stamps, molds, and conformable photomasks". Soft lithography uses elastomeric materials, such as, for example polydimethylsiloxane (PDMS). Soft lithography is generally used to construct features measured on the micrometer to nanometer scale.

As used herein, the term "photoresist" means a light-sensitive material used in several industrial processes, such as photolithography and photoengraving to form a patterned coating on a surface. A positive photoresist is a type of photoresist in which the portion of the photoresist that is exposed to light becomes soluble to the photoresist developer and the portion of the photoresist that is unexposed remains insoluble to the photoresist developer. A negative photoresist is a type of photoresist in which the portion of the photoresist that is exposed to light becomes relatively insoluble to the photoresist developer and the portion of the photoresist that is unexposed is dissolved by the photoresist developer.

As used herein, the term "micromachining" means a process used to produce micromachinery or microelectromechanical systems. Bulk micromachining produces structures inside a substrate.

As used herein, the expression "function generator" means a piece of electronic test equipment or software used to generate electrical waveforms. These waveforms can be either repetitive, or single-shot, in which case some kind of triggering source is required. As used herein, the expression "RE power amplifier" means a type of electronic amplifier used to convert a low-power radio-frequency signal into a larger signal of significant power, typically for driving the antenna of a transmitter. It is usually optimized to have high efficiency, high P1 dB compression, good return loss on the input and output, good gain, and good heat dissipation.

As used herein, the term "particle", includes, but is not limited to, particulate material in whole blood, such as, for example, red blood cells, white blood cells, and platelets.

Insofar as possible, like reference numerals will be used to designate like components.

Figure 3:
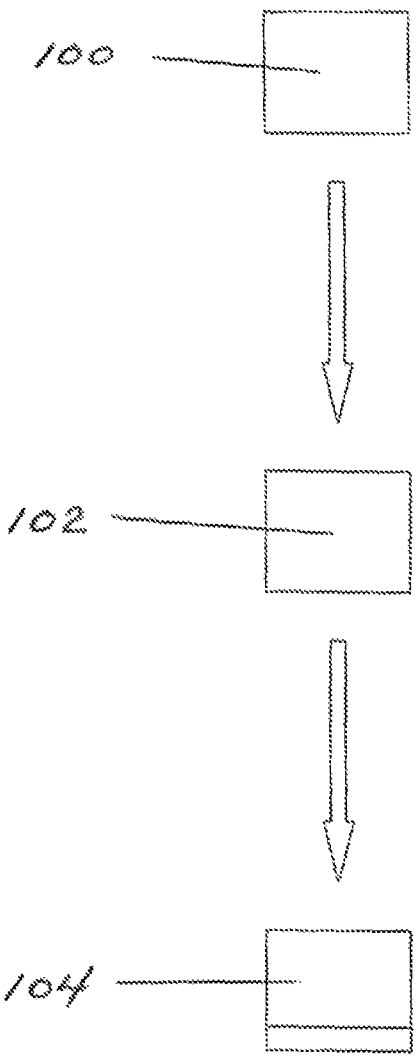
FIG. 3 is a block diagram illustrating a set of components that can be used to generate acoustic standing waves.
Figure 4:
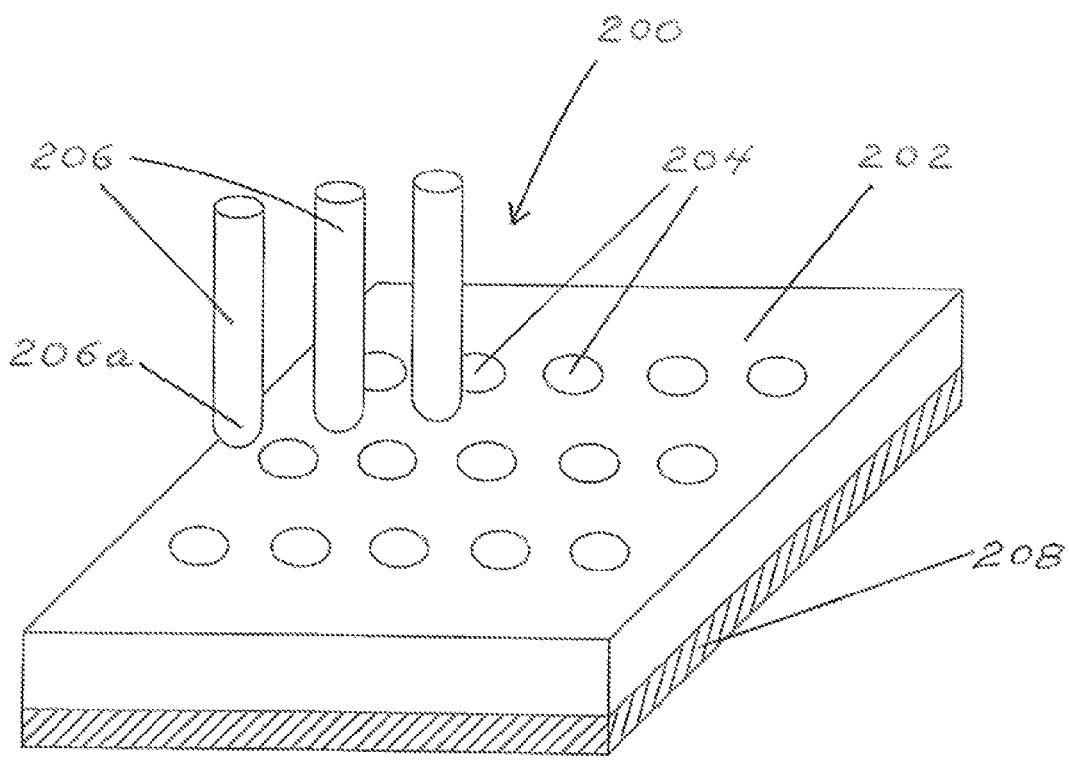
FIG. 4 is a perspective view of a plurality of tests tubes aligned with receptacles in an ultrasonic transducer assembly.
Figure 5:
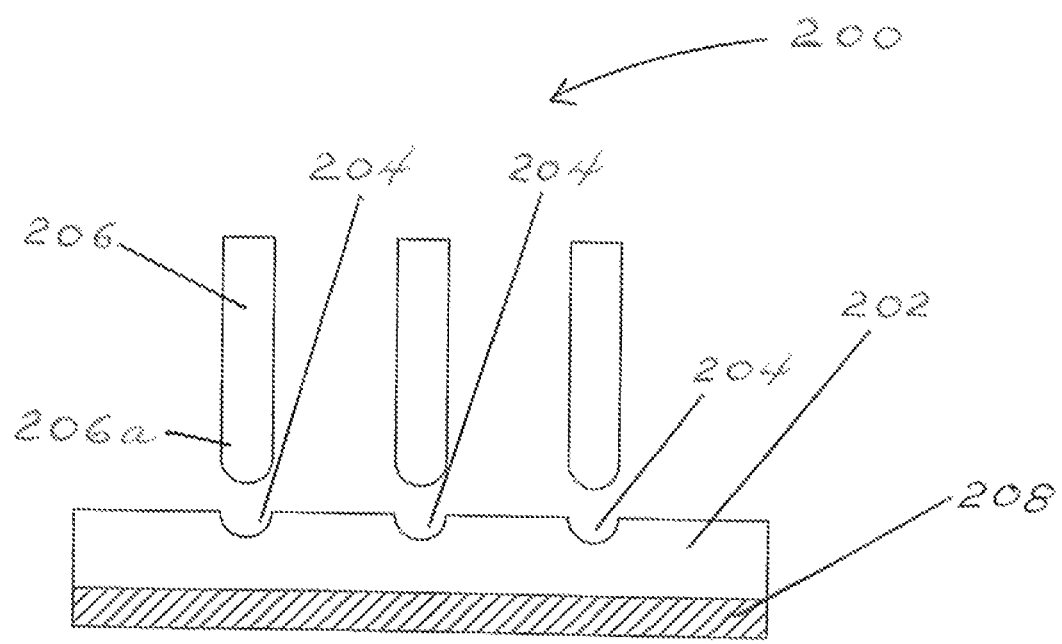
FIG. 5 is a cross-sectional view of the test tubes and the ultrasonic transducer assembly of FIG. 4.

A schematic diagram of the components that are used to generate acoustic standing waves is shown in FIG. 3. In FIG. 3, a function/waveform generator 100 provides a waveform or a standard function, e.g., a sine wave, a square wave, to a RF (radio frequency) power amplifier 102, which in turn provides amplification of the signal from the function/waveform generator 100 to an ultrasonic transducer 104. A representative example of a function/waveform generator 100 suitable for use herein is Agilent 33210A function/waveform generator, commercially available from Agilent Technologies. A representative example of a RF power amplifier 102 is IntraAction Model PA-4 RF power amplifier, commercially available from IntraAction Corp., Bellwood, Ill. A representative example of an ultrasonic transducer 104 is Olympus Accupath Wedge 45° Transducer, commercially available from Olympus NDT, Waltham, Mass. An ultrasonic transducer 104 can be custom-made by assembling components that are commercially available from Fuji Ceramics Corporation, Yamamia 2320-11, Fujinomiya-shi, Shizuoka-pref., Japan.

In the embodiment shown in FIGS. 4, 5, 6, and 7, an apparatus 200 for carrying out a batch process for effecting separation of blood cells from blood plasma or blood serum in a test tube or plurality of test tubes is shown. A layer 202 having at least one receptacle 204 for at least one test tube 206 functions as a delay line. The layer 202 is in face-to-face contact with a layer 208. The layer 208 functions as an acoustic energy transducer. The acoustic energy transducer 208 receives the appropriate function or waveform from the function/waveform generator 100, amplified by the RF (radio frequency) power amplifier 102, as shown in FIG. 3. The at least one receptacle 204 in the layer 202 has a shape that is congruent with the lower portion 206a of the at least one test tube 206.

Requirements and preferred features of a delay line are set forth in U.S. Pat. No. 3,832,655, incorporated herein by reference. Requirements and preferred features of acoustic energy transducers are set forth in Panametrics-NDT™ Ultrasonic Transducers Brochure 920-041C-EN, Olympus NDT, 2008, Waltham, Mass., pages 1-49, previously incorporated herein by reference.

Figure 6:
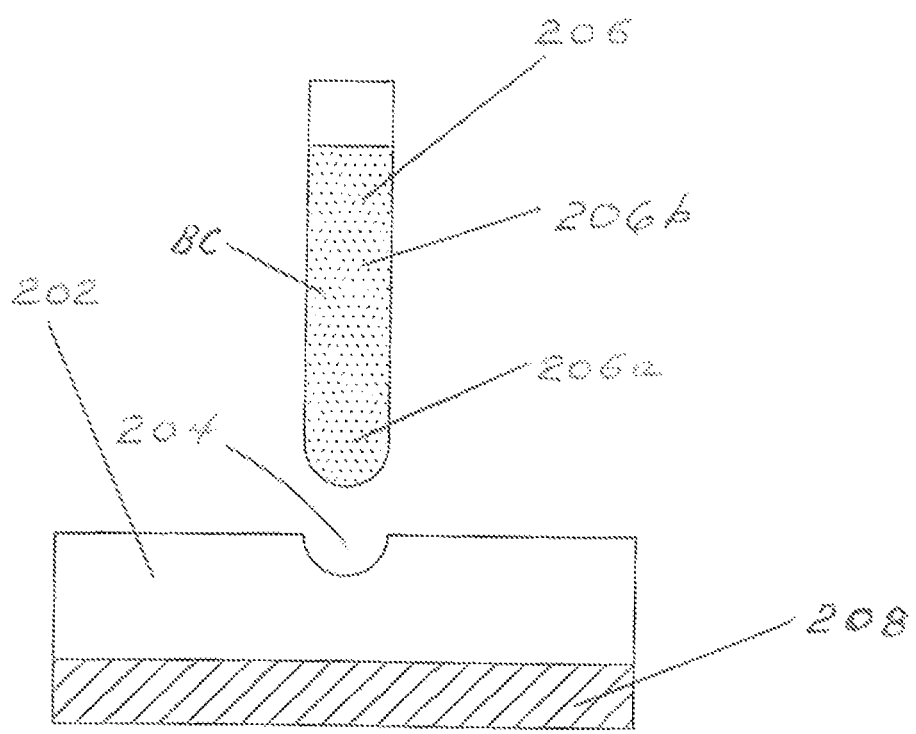
FIG. 6 is a cross-sectional view of a single test tube and a single receptacle in the ultrasonic transducer assembly, wherein the particles have not been separated.
Figure 7:
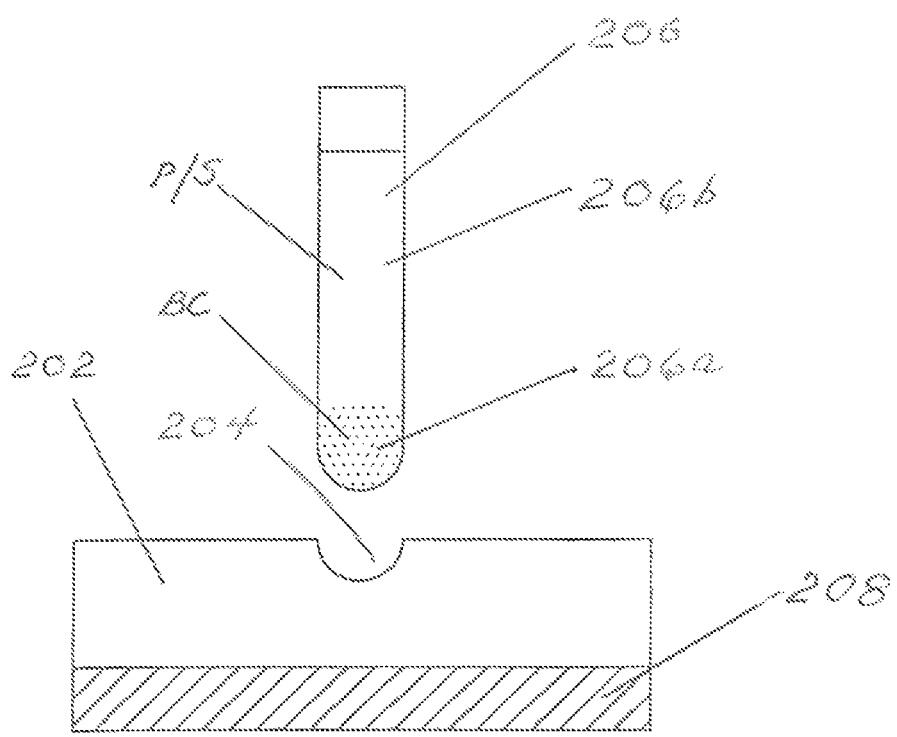
FIG. 7 is a cross-sectional view of a single test tube and a single receptacle in the ultrasonic transducer assembly, wherein the particles have been separated by acoustic energy.

The frequency can range from 20 KHz to 100 KHz. The frequency selected is based on the heights of the test tubes. A typical "VACUTAINER" test tube has the dimensions 13 mm (diameter)×75 mm (length). The frequency of 20 KHz generates an acoustic wave having a wavelength of 7 cm. The speed of sound in water is approximately 1450 m/sec. The acoustic node of the standing wave is placed at a location near the bottom of the test tube. The forces of the moving blood cells are acoustic, the primary force, and gravitational, the secondary force. The air serves as a reflective medium at the interface of blood and air, because of the large difference in acoustic impedance between air (close to zero) and blood ($1.483\times10^5$ g/cm$^2$ sec). Prior to the acoustic separation process, blood cells "BC" are substantially uniformly dispersed throughout the liquid in the test tube 206, as shown in FIG. 6. After the acoustic separation process, blood cells "BC" are concentrated in the lower layer 206a of the test tube 206 and plasma or serum "P/S" is presented in the upper layer 206b of the test tube 206, as shown in FIG. 7. The upper layer can then be removed from the test tube by manual aspiration, as by a pipette, or by robotic aspiration, as by a robotic pipette, for subsequent processes.

Figure 8:
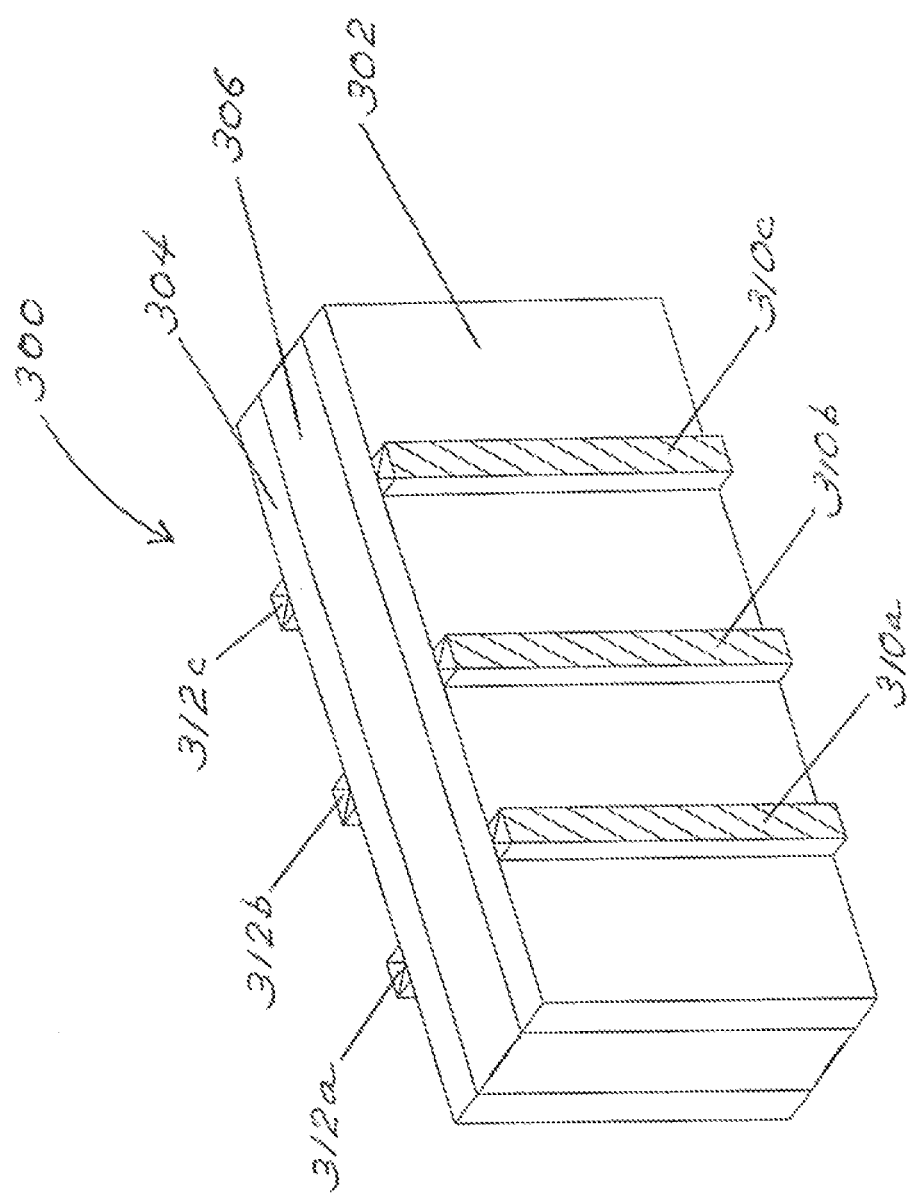
FIG. 8 is a perspective view of an assembly that contains a flow channel suitable for carrying out the method of separating blood cells from blood plasma or blood serum described herein.
Figure 9:
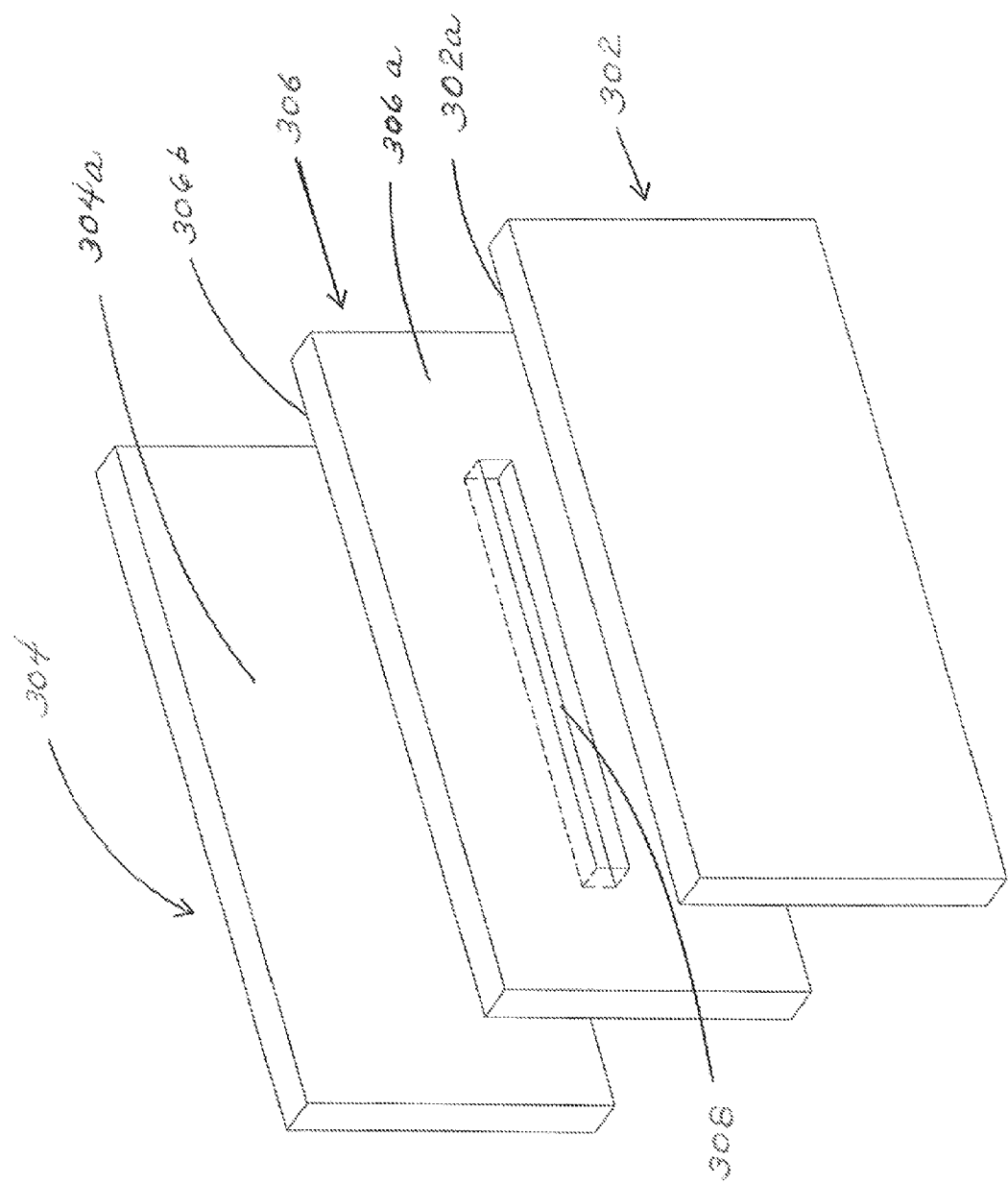
FIG. 9 is an exploded perspective view of the components that can be assembled to construct the assembly shown in FIG. 8.
Figure 10A:
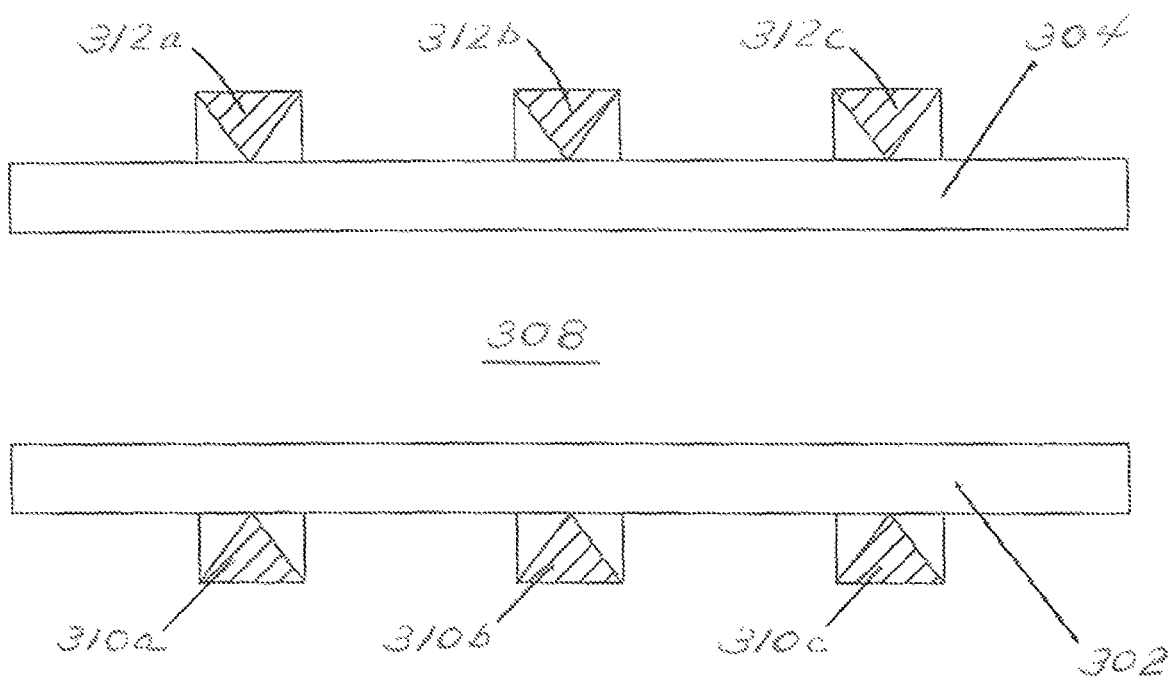
FIG. 10A is a top plan view of a flow channel suitable for use in separating particles from the liquid in which they are suspended by means of acoustic energy.
Figure 10B:
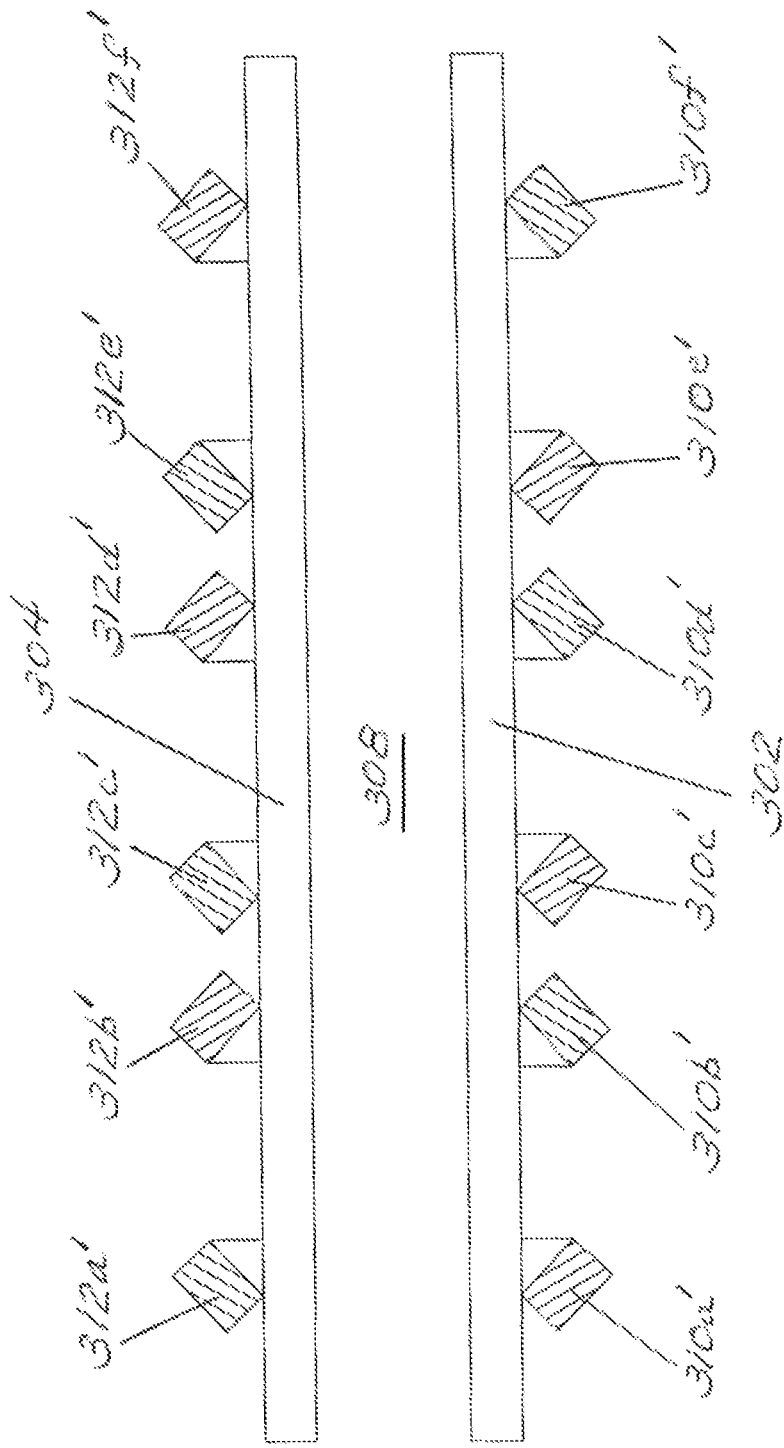
FIG. 10B is a top plan view of a flow channel suitable for use in separating particles from the liquid in which they are suspended by means of acoustic energy.
Figure 11A:
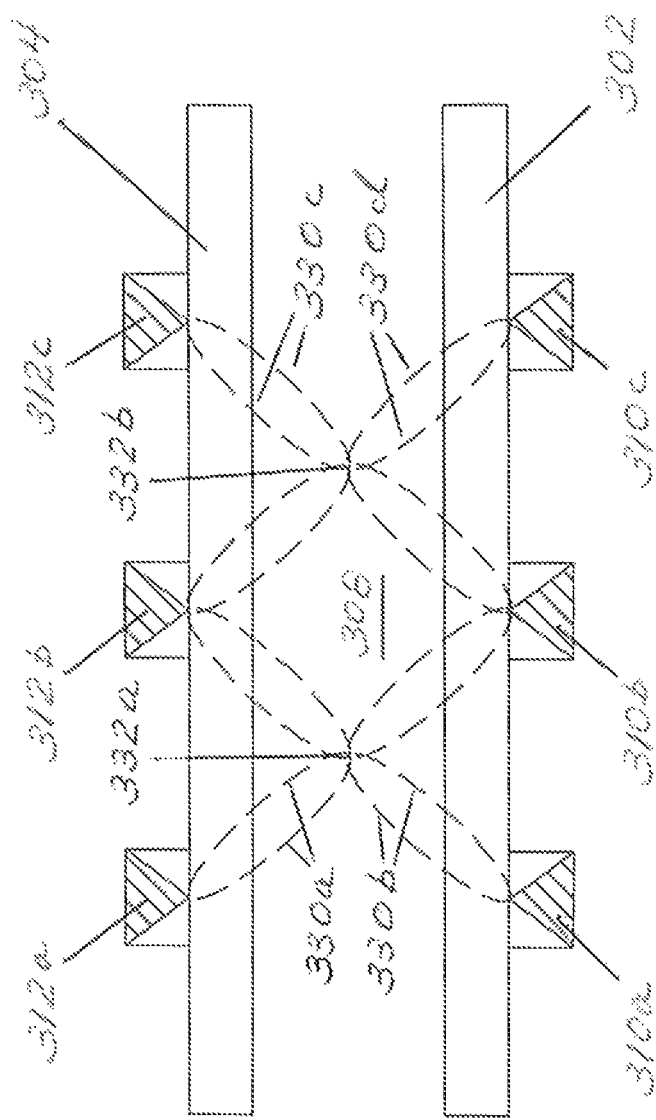
FIG. 11A is a top plan view of the flow channel of FIG. 10A.
Figure 11B:
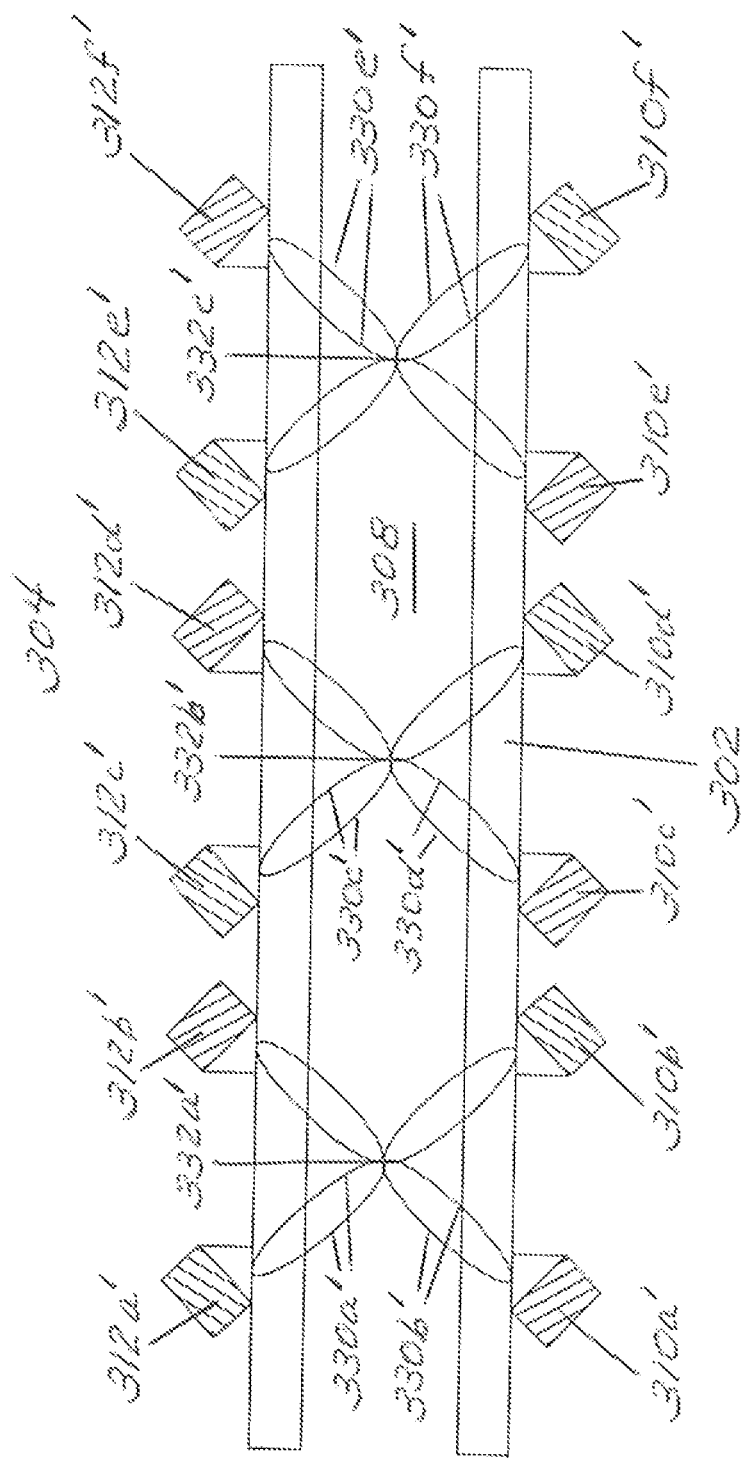
FIG. 11B is a top plan view of the flow channel of FIG. 10B.
Figure 11C:
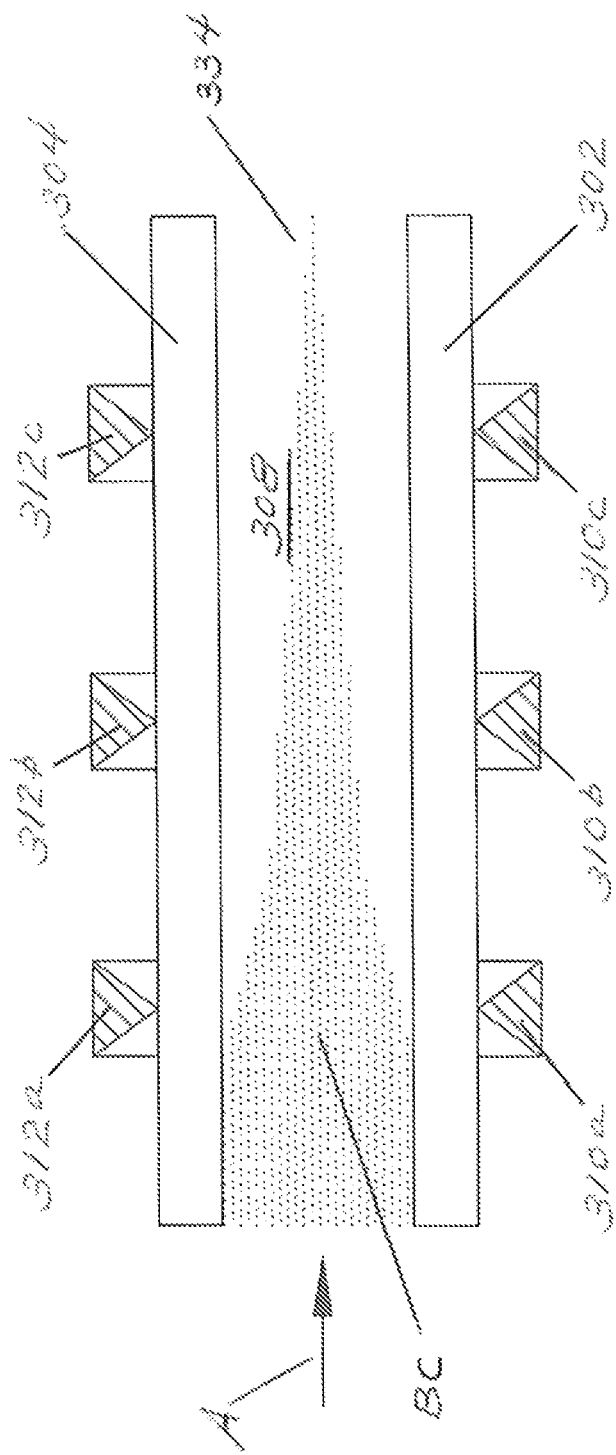
FIG. 11C is a top plan view of the flow channel of FIG. 10A.
Figure 11D:
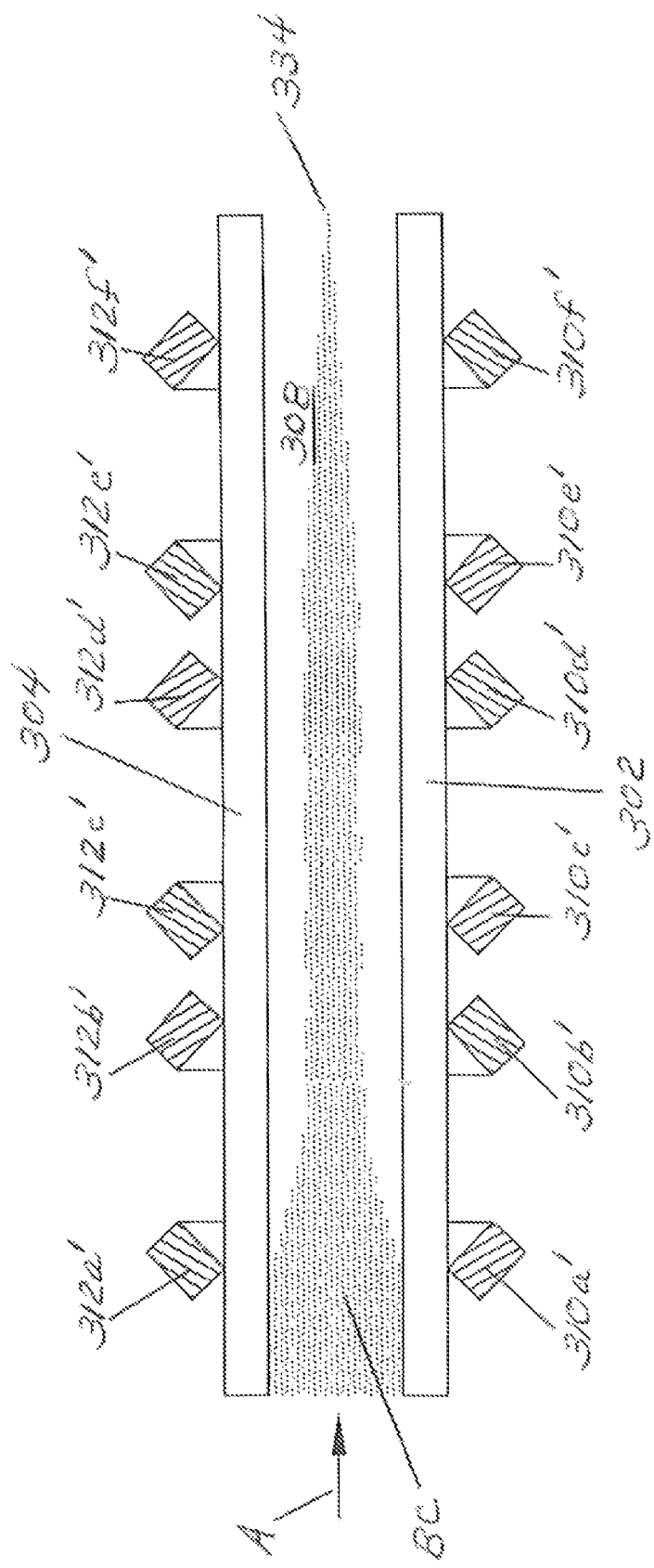
FIG. 11D is a top plan view of the flow channel of FIG. 10B.
Figure 16:
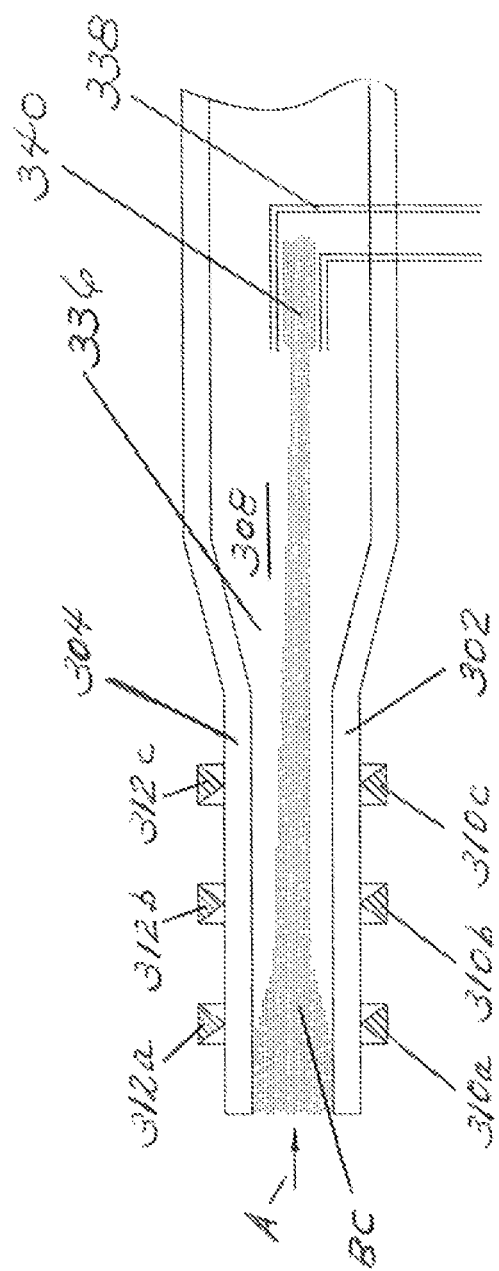
FIG. 16 is a top plan view of a flow channel, in which a conduit has been inserted to facilitate removal of particles.
Figure 17:
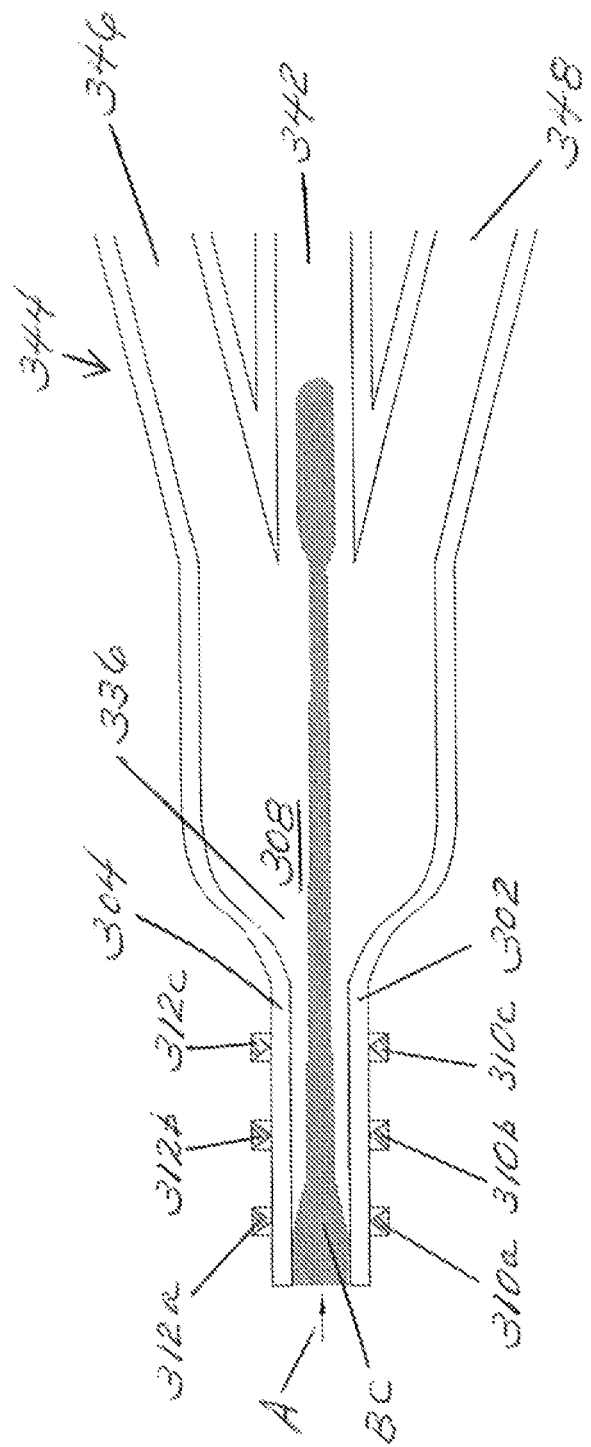
FIG. 17 is a top plan view of a flow channel, in which the flow channel has been divided into three sub-channels, whereby the blood cells are connected in the middle sub-channel and the blood plasma or blood serum is collected in the sub-channels that flank the middle sub-channel.

FIGS. 8, 9, 10A, 10B, 11A, 11B, 11C, 11D, 12, 13, 14, 15, 16, and 17 illustrate embodiments of articles that can be used to carry out a continuous process for effecting the separation of blood cells from blood plasma or blood serum in a flow channel. The flow channel is constructed with dimensions that allow the flow of the sample of blood to be laminar. FIGS. 8 and 9 illustrate how a flow channel can be constructed by combining three layers of material appropriate for preparing the apparatus described herein, wherein the two exterior layers form boundaries of the flow channel and the flow channel itself is formed in the interior layer. FIG. 10A illustrates a flow channel that employs a set of custom-designed ultrasonic transducers, which are indicated by triangular cross-sections. FIG. 10B illustrates a flow channel that employs a set of commercially available ultrasonic transducers, which are indicated by rectangular cross-sections. FIG. 11A illustrates acoustic standing waves generated by the ultrasonic transducers shown in FIG. 10A. FIG. 11B illustrates acoustic standing waves generated by the ultrasonic transducers shown in FIG. 10B, FIG. 11C illustrates particles, e.g., blood cells and platelets, flowing parallel to the walls of the flow channel of FIG. 10A. FIG. 11D illustrates particles, e.g., blood cells and platelets, flowing parallel to the walls of the flow channel of FIG. 10B. FIGS. 12, 13, 14, and 15 illustrate various embodiments of inlet channels leading into and outlet channels leading out of the flow channel described herein. FIGS. 16 and 17 illustrate alternative means for removing blood cells from flow channels.

FIG. 8 shows an article 300 having a flow channel suitable for use for the method described herein. FIG. 9 shows an exploded view of the article 300 shown in FIG. 8. Referring now to FIGS. 8 and 9, the article 300 comprises a first exterior layer 302, a second exterior layer 304, and an interior layer 306. One major surface 306a of the interior layer 306 is in face-to-face contact with one major surface 302a of the first exterior layer 302 and the other major surface 306b of the interior layer 306 is in face-to-face contact with one major surface 304a of the second exterior layer 304. A flow channel 308 is an aperture cut through the interior layer 306. As shown in FIGS. 8 and 9, the major surface 302a of the first exterior layer 302 and the major surface 304a of the second exterior layer 304 are spaced apart by means of the interior layer 306 to form a flow channel 308. If the flow channel is merely cut into a major surface of the interior layer 306, the first exterior layers 302 or the second exterior layer 304 can be dispensed with. The layers 302 and 304 also function as delay lines. The delay lines provide a means for removing unstable near field acoustic effects. The sound field of an ultrasonic transducer is divided into two zones, the near field and the far field. The near field is the region directly in front of the ultrasonic transducer where the echo amplitude goes through a series of maxima and minima and ends at the last maximum, at a distance N from the ultrasonic transducer. The location of the last maximum is known as the near field distance and is the natural focus of the ultrasonic transducer. The far field is the area beyond N where the sound field pressure gradually drops to zero. The near field effect is a phenomenon resulting from the geometry of the ultrasonic transducer. The sound that emanates from an ultrasonic transducer does not originate from a point, but rather from most of the surface of the ultrasonic transducer. Sound waves from the surface of the ultrasonic transducer create diffraction effects on account of interference of the sound waves. Extensive fluctuation in the intensity of the sound near the source of the sound waves is referred to as near field effects. Near field effects are discussed in greater detail in Panametrics-NDT™ Ultrasonic Transducers Brochure 920-041C-EN, 2008, Olympus NDT, Waltham, Mass., pages 1-49, previously incorporated herein by reference.

The flow channel 308 is preferably elongated, in order to provide a satisfactory rate of flow with a small volume of the sample. Representative examples of the dimensions of the flow channel 308 can range from about 30 mm to about 60 mm in length (i.e., the direction of flow of the fluid), from about 70 μm to about 700 μm, preferably from about 100 μm to about 200 μm, in width (i.e., the direction perpendicular to the walls of the flow channel upon which the ultrasonic transducers are mounted), and from about 1000 μm to about 5000 μm in depth (i.e., the direction parallel to the walls of the flow channel upon which the ultrasonic transducers are mounted). The depth is selected to be of such a magnitude as to minimize the effect of gravitational force on the blood cells' and the platelets. The selection of the width of the flow channel 308 is based upon the frequency selected. The frequency and width of the flow channel 308 are selected in such a manner as to drive the blood cells to the center of the flow channel 308. For example, a frequency of approximately 7.5 MHz calls for a width of the flow channel 308 of approximately 100 μm, and a frequency of approximately 3.5 MHz calls for a width of the flow channel 308 of approximately 200 μm. The major surface 302a of the first exterior layer 302 can be joined to the major surface 306a of the interior layer 306 by means of adhesives or anodic bonding. The major surface 304a of the second exterior layer 304 can be joined to the major surface 306b of the interior layer 306 by means of adhesives or anodic bonding. The distance between the major surface 302a of the first exterior layer 302 and the major surface 304a of the second exterior layer 304, which constitutes the width of the flow channel 308, can range from about 70 μm to about 700 μm, preferably from about 100 μm to about 200 μm.

The perpendicular distance between the edges of the flow channel 308 that are parallel to the direction of the flow of the fluid in the flow channel 308 is preferably greater than about 1000 μm, in order to provide an adequate level of throughput. The length of the flow channel is preferably greater than about 30 mm, in order to provide an adequate level of throughput. A plurality of ultrasonic transducers 310a, 310b, and 310c are coupled with the layer 302 and a plurality of ultrasonic transducers 312a, 312b, and 312c are coupled with the layer 304. The ultrasonic transducers 310a, 310b, 310c, 312a, 312b, and 312c are arranged so that the incident angle of the wave relative to the first exterior layer 302 and the second exterior layer 304 is approximately 45°. Additional ultrasonic transducers (not shown) can be used. It is also possible to use fewer ultrasonic transducers. As shown in FIGS. 8, 10A, 11A, and 11C, the ultrasonic transducers 310a, 310b, 310c, 312a, 312b, and 312c, which have triangular cross-sections, are custom-designed ultrasonic transducers. As shown in FIGS. 10B, 11B, and 11D, the ultrasonic transducers 310a', 310b', 310c', 310d', 310e', 310f', 312a', 312b', 312c', 312d', 312e', and 312f', which have rectangular cross-sections, are commercially available ultrasonic transducers. The arrangement of the ultrasonic transducers 310a, 310b, 310c, 312a, 312b, and 312c enables refraction and reflection of sound waves and the formation of standing waves 330a, 330b, 330c, 330d with nodes 332a and 332b at the center of the flow channel 308. The arrangement of the ultrasonic transducers 310a', 310b', 310c', 310d', 310e', 310f', 312a', 312b', 312c', 312d', 312e', and 312f' enables refraction and reflection of sound waves and the formation of standing waves 330a', 330b', 330c', 330d', 330e', and 330f' with nodes 332a', 332b', 332c' at the center of the flow channel 308. When a sample of whole blood flows through the flow channel 308 in the direction indicated by the arrow "A", blood cells, indicated by "BC" are concentrated in a central zone 334 of the flow channel 308 by acoustic energy.

Figure 12:
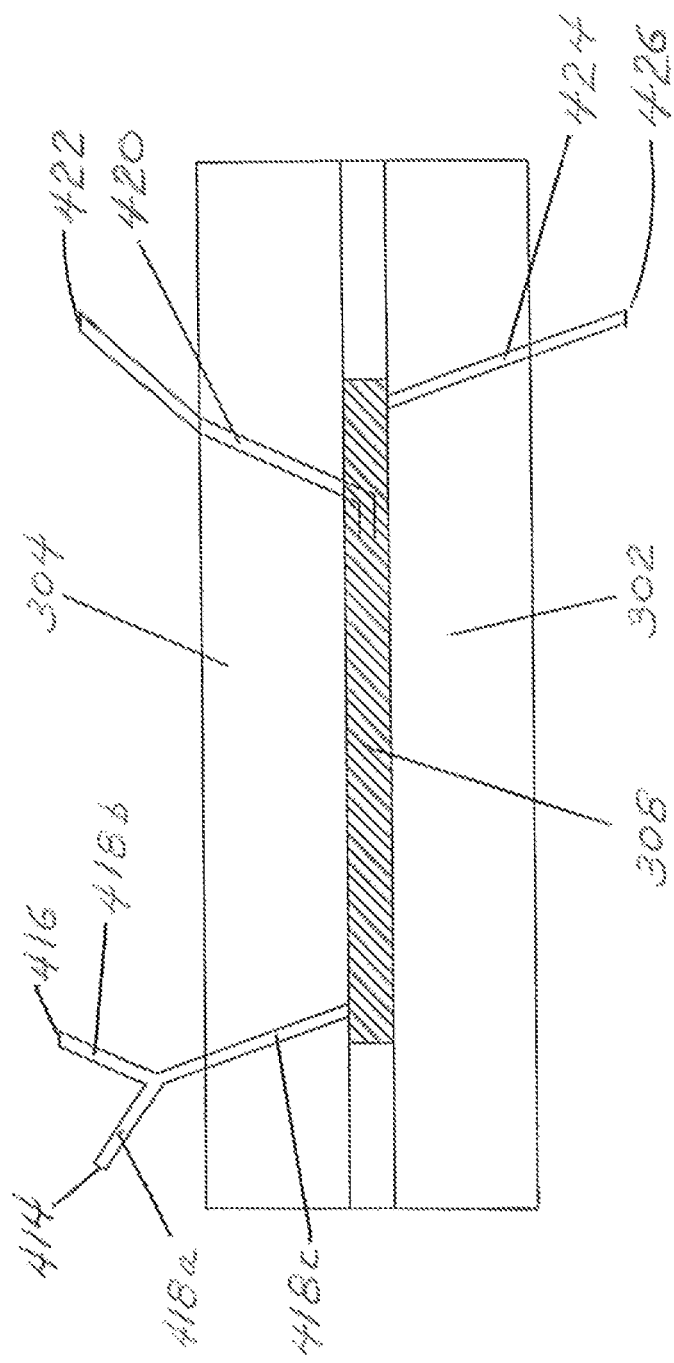
FIG. 12 is a top plan view of an embodiment of the flow channel of FIG. 11, further showing an inlet channel by means of which a sample of blood can be introduced into the flow channel and two outlet channels by means of which components of a sample of blood can be removed from the flow channel.
Figure 13:
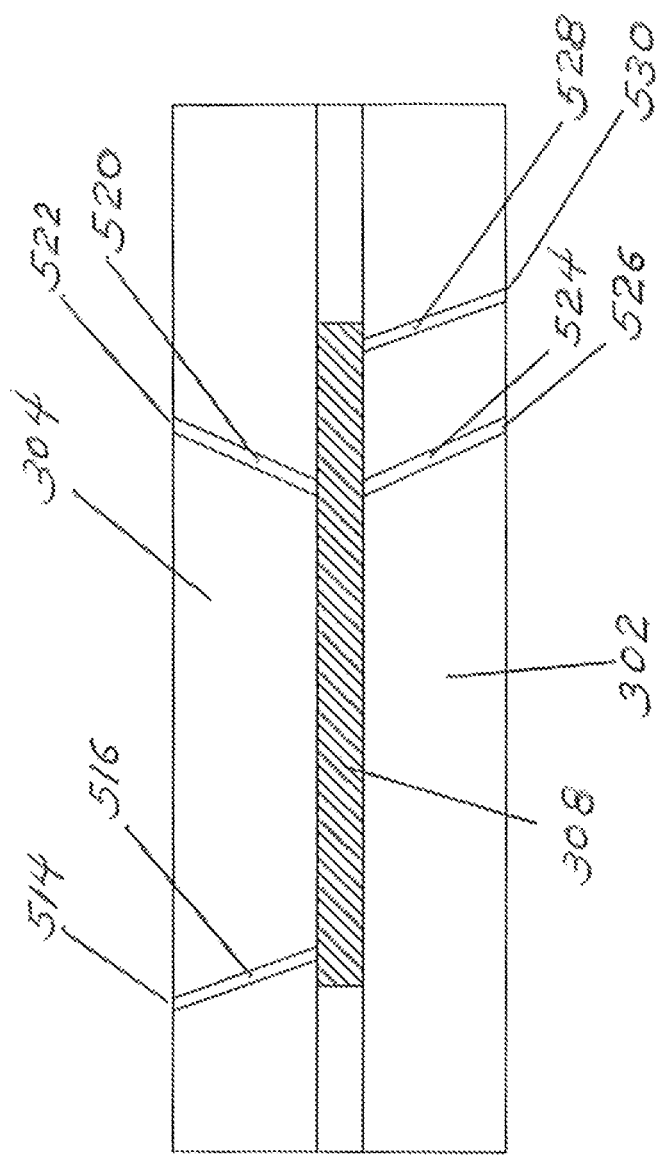
FIG. 13 is a top plan of another embodiment of the flow channel of FIG. 11, further showing one inlet channel by which a sample of blood can be introduced into the flow channel and three outlet channels by means of which components of a sample of blood can be removed from the flow channel.
Figure 14:
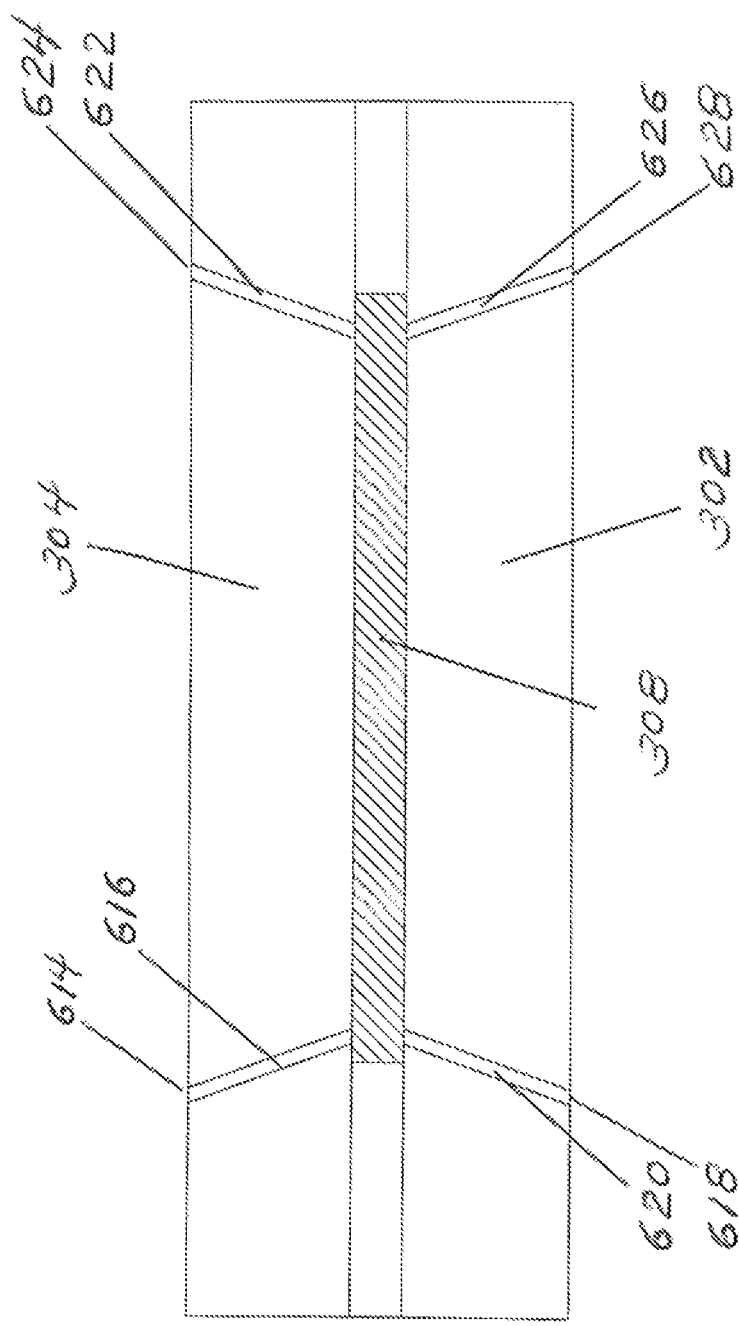
FIG. 14 is a top plan view of the still another embodiment of FIG. 11, further showing two inlet channels by means of which a sample of blood can be introduced into the flow channel and two outlet channels by means of which components of a sample of blood can be removed from the flow channel.
Figure 15:
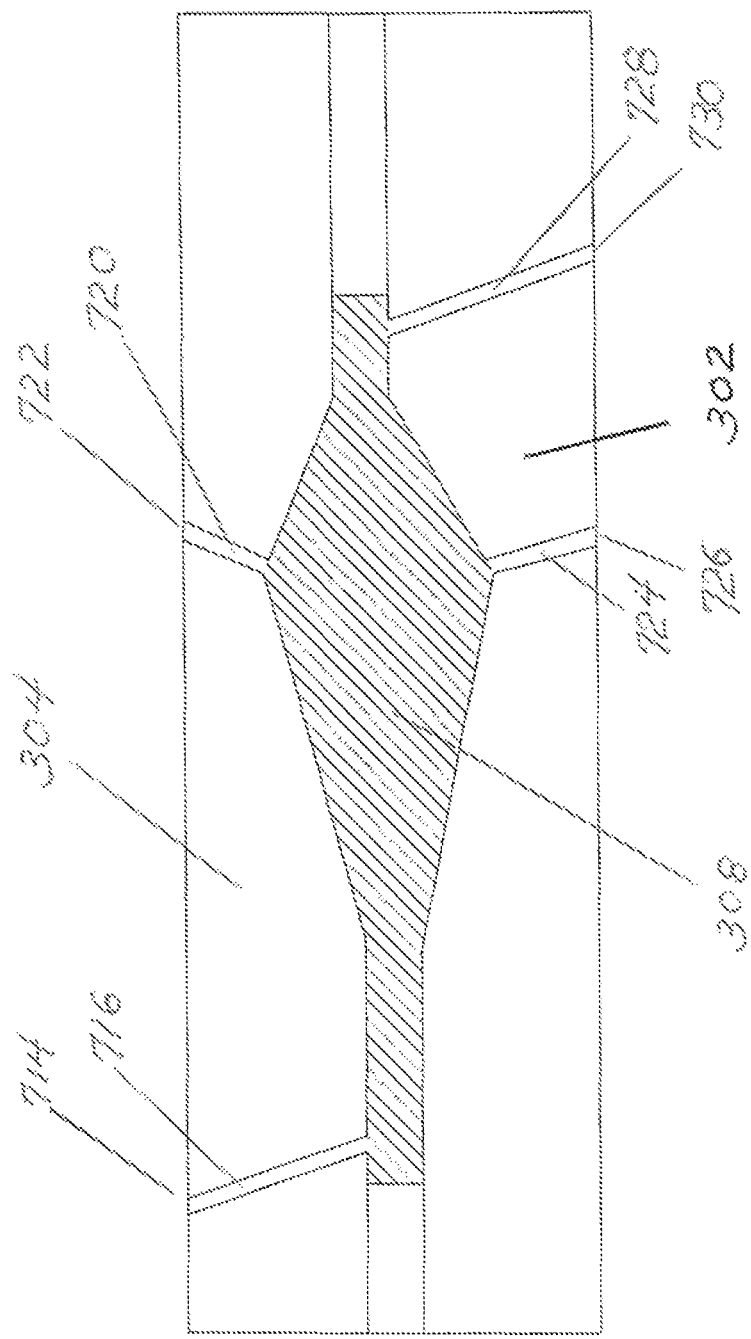
FIG. 15 is a top plan view of still another embodiment of FIG. 11, further showing one inlet channel by means of which a sample of blood can be introduced into the flow channel and three outlet ports channels by means of which a sample of blood can be removed from the flow channel.

FIGS. 12, 13, 14, and 15 illustrate various inlet ports and inlet channels by means of which a sample of whole blood can be introduced into the flow channel 308 along with various outlet ports and outlet channels by means of which blood cells and blood plasma or blood serum can be removed from the flow channel 308. It should be noted that for the sake of simplification, the ultrasonic transducers are not shown in FIGS. 12, 13, 14, and 15. In FIGS. 12, 13, 14, and 15, the parallel, hatched lines represent the fluid in the flow channel 308. In FIG. 12, a first inlet port 414 and a second inlet port 416 communicate with the flow channel 308 by means of inlet channels 418a, 418b, and 418c. The inlet channel 418c is formed in the second exterior layer 304. A sample of whole blood can be introduced into the flow channel 308 by introducing the sample into the first inlet port 414, the second inlet port 416, or both inlet ports 414 and 416. Buffers can also be introduced into the flow channel 308 by introducing the buffers into the first inlet port 414, the second inlet port 416, or both inlet ports 414 and 416. A first outlet channel 420 is formed in the second exterior layer 304. The first outlet channel 420 enables removal of blood cells from the flow channel 308 by means of a first outlet port 422. A second outlet channel 424 is formed in the first exterior layer 302. The second outlet channel 424 enables removal of blood plasma or blood serum from the flow channel 308 by means of a second outlet port 426. In FIG. 12, it can be seen that the inlet channels 418a, 418b, and 418c and the outlet channels 420 and 424 extend beyond the outermost faces of the first exterior layer 302 and the second exterior layer 304. In FIGS. 13, 14, and 15, the inlet channels and the outlet channels terminate at the outermost faces of the first exterior layer 302 and the second exterior layer 304.

In FIG. 13, an inlet port 514 communicates with the flow channel 308 by means of an inlet channel 516. The inlet channel 516 is formed in the second exterior layer 304. A sample of whole blood can be introduced into the flow channel 308 by introducing the sample into the inlet port 514. Buffers can also be introduced into the flow channel 308 by introducing the buffers into the inlet port 514. A first outlet channel 520 is formed in the second exterior layer 304. The first outlet channel 520 enables removal of blood plasma or blood serum from the flow channel 308 by means of a first outlet port 522. A second outlet channel 524 is formed in the first exterior layer 302. The second outlet channel 524 enables removal of blood plasma or blood serum from the flow channel 308 by means of a second outlet port 526. A third outlet channel 528 is formed in the first exterior layer 302. The third outlet channel 528 enables removal of blood cells and platelets from the flow channel 308 by means of a third outlet port 530.

In FIG. 14, a first inlet port 614 communicates with the flow channel 308 by means of a first inlet channel 616. The first inlet channel 616 is formed in the second exterior layer 304. A second inlet port 618 communicates with the flow channel 308 by means of a second inlet channel 620. The second inlet channel 620 is formed in the first exterior layer 302. A sample of whole blood can be introduced into the flow channel 308 by introducing the sample into the first inlet port 614, the second inlet port 618, or both inlet ports 614 and 618. Buffers can also be introduced into the flow channel 308 by introducing the buffers into the first inlet port 614, the second inlet port 618, or both inlet ports 614 and 618. A first outlet channel 622 is formed in the first exterior layer 302. The first outlet channel 622 enables removal of blood plasma or blood serum from the flow channel 308 by means of a first outlet port 624. A second outlet channel 626 is formed in the first exterior layer 302. The second outlet channel 626 enables removal of blood plasma or blood serum from the flow channel 308 by means of a second outlet port 628.

In FIG. 15, an inlet port 714 communicates with the flow channel 308 by means of an inlet channel 716. The inlet channel 716 is formed in the second exterior layer 304. A sample of whole blood can be introduced into the flow channel 308 by introducing the sample into the inlet port 714. Buffers can also be introduced into the flow channel 308 by introducing the buffers into the inlet port 714. A first outlet channel 720 is formed in the second exterior layer 304. The first outlet channel 720 enables removal of blood plasma or blood serum from the flow channel 308 by means of and the first outlet port 722. A second outlet channel 724 is formed in the first exterior layer 302. The second outlet channel 724 enables removal of blood plasma or blood serum from the flow channel 308 by means of a second outlet port 726. A third outlet channel 728 is formed in the first exterior layer 302. The third outlet channel 728 enables removal of blood cells and platelets from the flow channel 308 by means of a third outlet port 730. The width of the flow channel 308 in FIG. 15 increases between the first inlet channel 716 and both the first outlet channel 720 and the second outlet channel 724. The width of the flow channel 308 in FIG. 15 decreases between the third outlet channel 728 and both the first outlet channel 720 and the second outlet channel 724.

Requirements and preferred features of a delay line are set forth in U.S. Pat. No. 3,832,655, incorporated herein by reference. Requirements and preferred features of acoustic energy transducers are set forth in Panametrics-NDT™ Ultrasonic Transducers Brochure 920-041C-EN, 2008, Olympus NDT, Waltham, Mass., pages 1-49, previously incorporated herein by reference.

The frequency can range from about 1 MHz to about 10 MHz, preferably from about 3 MHz to about 6 MHz. At a collection zone 336 of the flow channel 308, the width of the flow channel 308 is expanded gradually to maintain laminar flow of the sample and avoid turbulence. The expanded width of the collection zone 336 facilitates the collection of blood cells and the collection of serum and plasma. As shown in FIG. 16, blood cells can be removed by inserting a conduit 338 at the central zone 340 of the flow channel 308 in the center of the collection zone 336. Alternatively, as shown in FIG. 17, blood cells can be removed by creating a central outlet 342 at the distal end 344 of the flow channel 308. The blood plasma or the blood serum can be removed through the outlets 346 and 348, which flank the central outlet 342. The plurality of ultrasonic transducers 310a, 310b, 310c, 312a, 312b, 312c along the flow channel 308 should be oriented so that the gravitational forces do not adversely affect the separation of blood cells from blood plasma or blood serum.

The apparatus described herein and the components of the apparatus described herein can be formed from a variety of sub-components. Samples and buffer solutions can be moved though the inlet flow channels and the outlet flow channels illustrated in FIGS. 12, 13, 14, and 15 and the flow channel 308 by means of positive displacement pumps, such as, for example, syringe pumps, peristaltic pumps. The flow channel 308 can be formed in the interior layer 306 by any of several processes. In one process, a silicon wafer can be used for preparing the interior layer 306. The flow channel 308 can be formed in the silicon wafer by micromachining, anisotropic wet etching, or by deep reactive ion etching. Inlet channels, inlet ports, outlet channels, and outlet ports or recesses for receiving inlet channels, inlet ports, outlet channels, and outlet ports can also be formed in silicon wafers by micromachining, anisotropic wet etching, or by deep reactive ion etching. Micromachining can be carried out by any of the methods described in the article located at the web site http://en.wikipedia.orq/wiki/Bulk_micromachining, incorporated herein by reference. Anisotropic wet etching can be performed with potassium hydroxide or EDP solution, which is a mixture of ethylene diamine and pyrocatechol. The portion of the silicon wafer that is not to be etched is masked by a photoresist, which has been applied in a desired pattern by a photolithographic process. A negative photoresist suitable for use is epoxy-based SU-8, commercially available from Microchem, Newton, Mass. Deep reactive ion etching can be carried out by plasma etching.

In another process, the flow channel 308 can be micromolded by means of a high melt flow thermoplastic resin, wherein the melt flow index is equal to or greater than 20. Resins suitable for this technique include, but are not limited to, acrylic resins, polystyrene, polycarbonate, cyclo-olefin copolymers, and polyvinyl chloride.

In still another process, the flow channel 308 can be prepared by soft lithography, wherein a negative photoresist is employed and the pattern stamp is formed with polydimethylsiloxane. A commercially available polydimethylsiloxane suitable for use in this process is "SYLGARD" 184 Silicone Elastomer, Dow Corning Corporation.

The first exterior layer 302 and the second exterior layer 304 are preferably made of optically and acoustically transparent material. Such materials include, but are not limited to, (a) glass, such as, for example, polysilicate glass, e.g., "PYREX" glass, "PYREX" 7740 Glass, (b) silicon wafer, and (c) polymeric materials, such as, for example, acrylic resins, polystyrene, polycarbonate, cyclo-olefin copolymers, and polyvinyl chloride.

The major surface 302a of the first exterior layer 302 can be bonded to the major surface 306a of the interior layer 306 and the major surface 304a of the second exterior layer 304 can be bonded to the major surface 306b of the interior layer 306 by means of adhesives, such as, for example, two-part epoxy adhesives, two-part urethane adhesives. The major surface 302a of the first exterior layer 302 can be bonded to the major surface 306a of the interior layer 306 and the major surface 304a of the second exterior layer 304 can be bonded to the major surface 306b of the interior layer 306 by means of anodic bonding, which requires high voltage, e.g., greater than 1000 volts, and high temperature, greater than 250° C. A commercially available power supply is DC High Voltage Power Supply, Model PS310, commercially available from Stanford Research Systems.

The inlet ports and the outlet ports can be machined by means of screw threads, after which machining process port adapters can be inserted in the ports. Tubing connections can be effected by means of glue, interference fit, or solvent bonding. Solvent bonding is preferred for polyvinyl chloride tubing. Materials that are suitable for tubing include, but are not limited to, polyvinyl chloride, silicone, polytetrafluoroethylene, ultra low density polyethylene.

Separation efficiency depends on the particle size, the acoustic frequency, and the energy density of the acoustic standing waves. Commercially available piezoelectric elements, such as PZT (lead zirconate titanate), can be used to generate acoustic waves.

The dimensions of the flow channel 308 need to be adjusted to facilitate laminar flow. Optimal separation can be achieved by adjusting one half of the wavelength to be the same width of the flow channel 308, thereby allowing for the node to be aligned in the center of the flow channel 308 and antinodes to be adjacent to the walls of the flow channel, whereby cells accumulate at the center of the flow channel 308. Alternatively, optimal separation can be achieved by adjusting quarter wavelength with a node adjacent to one wall of the flow channel and an antinode adjacent to the opposing wall of the flow channel, whereby cells accumulate at the walls of the channel. For a continuous separation process, the positions of the nodes and antinodes of acoustic standing waves determine the location(s) where blood cells, platelets, and blood plasma or blood serum can be collected. The frequency required is in the ultrasound domain (>20,000 Hz), so the wavelength is matched with the dimensions of the flow channel 304.

The plurality of ultrasonic transducers is preferably oriented with respect to the flow channel so that gravitational forces do not adversely affect the separation. See FIG. 8.

Removal of blood cells can be facilitated by the addition of a buffer, e.g., phosphate buffered saline, to the sample of whole blood. Laminar flow prevents intermixing of fluid streams, whereby blood plasma or blood serum can be collected at a location different from that where blood cells are collected.

Ultrasonic transducers are commonly manufactured with piezoelectric materials, such as lead zirconate titanate (PZT) or polyvinylidene fluoride, or magnetorestrictive materials, such as rare earth alloy, Terfenol-D.

The apparatus and methods described herein have numerous benefits. The apparatus described herein requires a smaller amount of space than do other types of separating equipment. The apparatus described herein costs less than do other types of separating equipment, such as, for example, centrifuges. Moreover, the cost of maintenance of the apparatus described herein is much lower than that of other types of separating equipment, such as, for example, centrifuges.

OPERATION

In order to operate the apparatus shown in FIGS. 4, 5, 6, and 7, a sample of whole blood is introduced into a test tube 206. Prior to the acoustic separation process, blood cells "BC" are substantially uniformly dispersed throughout the liquid in the test tube 206, as shown in FIG. 6. A standing acoustic wave is then generated in such a manner by the function/waveform generator 100, the RF (radio frequency) power amplifier 102, and the ultrasonic transducer assembly, which comprises the delay line 202 and the acoustic energy transducer 208, that the acoustic node of the standing wave is placed at a location near the bottom of the test tube. The forces of the moving blood cells are acoustic, the primary force, and gravitational, the secondary force. Air serves as a reflective medium at the interface of blood and air, because large differences of acoustic impedances between air and the sample of blood, because large differences of acoustic impedances between air (close to zero) and blood ($1.483 \times 10^5$ g/cm² sec). After the acoustic separation process, blood cells "BC" are concentrated in the lower layer 206a of the test tube 206 and plasma or serum "P/S" is presented in the upper layer 206b of the test tube 206, as shown in FIG. 7. The upper layer can then be removed from the test tube by manual aspiration, as by a pipette, or by robotic aspiration, as by a robotic pipette, for subsequent processes.

In order to operate the apparatus shown in FIGS. 8, 9, 10A, 10B, 11A, 11B, 11C, 11D, 12, 13, 14, 15, 16, and 17, a sample of whole blood is introduced into the flow channel 308, typically by means of an inlet port and an inlet channel. Standing acoustic waves are then generated in such a manner by the function/waveform generator 100, the RF (radio frequency) power amplifier 102, the ultrasonic transducers 310a, 310b, 310c, 310a', 310b', 310c', 310d', 310e', 310f, 312a 312b, 312c, 312a', 312b', 312c', 312d', 312e', and 312f' that the nodes are formed in the center of the flow channel 308, i.e., equidistant from the walls, i.e., the first exterior layer 302 and the second exterior layer 304 of the flow channel 308. The red blood cells, the white blood cells, and the platelets, i.e., "BC", are concentrated at the nodes that are formed in the center of the flow channel 308 as the sample flows through the flow channel 308. The red blood cells, the white blood cells, and the platelets, i.e., "BC", can be removed by one outlet channel or by one conduit, and the blood plasma or the blood serum can be removed by at least one other outlet channel or by at least one other conduit.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for removing particles from a sample of fluid comprising a particulate component suspended in a liquid component, said method comprising:
   providing a sample of fluid;
   introducing the sample of fluid into an apparatus, the apparatus comprising:
      a flow channel defined by a first layer and a second layer, the flow channel comprising:
         a first section having a first width;
         a second section having a cross section that increases to a second width, then decreases to a third width; and
         a third section having the third width, a first end of the second section coupled to the first section and a second end of the second section coupled to the third section;
      an inlet channel extending through one of the first layer or the second layer and coupled to the first section;
      a first outlet channel extending through one of the first layer or the second layer and coupled to the second section; and
      a second outlet channel extending through one of the first layer or the second layer and coupled to the third section;
   providing an acoustic field within the flow channel, which field contains acoustic standing waves generated by external ultrasonic transducers;
   maintaining a laminar flow of the sample of fluid in the flow channel;
   removing near field acoustic effects;
   separating the particulate component from the liquid component; and
   collecting the liquid component.

2. The method of claim 1 further comprising manipulating the particulate component with the acoustic standing waves generated by the ultrasonic transducers without contacting the particulate component.

3. The method of claim 1, wherein the acoustic standing waves maintain acoustic nodes and antinodes in different layers of the flow of the sample of fluid.

4. The method of claim 1, wherein the particulate component and the liquid component migrate differentially to areas of preferred acoustic interaction.

5. The method of claim 1, wherein the particulate component comprises blood cells and the liquid component comprises at least one of blood plasma or blood serum, and wherein at least one of a size, a density or a compressibility of the blood cells or the at least one of blood plasma or blood serum affect the separation of the blood cells from the at least one of blood plasma or blood serum.

6. The method of claim 1 further comprising constructing the flow channel to enable the laminar flow of the sample of fluid.

7. The method of claim 1, wherein the first layer and second layer are parallel or substantially parallel and form walls of the flow channel.

8. The method of claim 7, wherein the walls are separated a distance greater than about 1000 μm and a length of the flow channel is greater than about 30 mm.

9. The method of claim 1, wherein removing unstable near field acoustic effect comprises use of a delay line.

10. The method of claim 9, wherein the transducers and the delay line are attached to the flow channel to cause an incident angle of the wave relative to the wall to be approximately 45°.

11. The method of claim 1, wherein at least one of the first layer or the second layer of the flow channel is a delay channel.

12. The method of claim 11, wherein collecting the liquid component comprises removing the liquid component via the first outlet channel of the flow channel.

13. The method of claim 1 further comprising using refraction and reflection of sound waves and the standing waves with nodes at a center of the flow channel for one or more of providing the acoustic field, maintaining the laminar flow or separating the particulate component from the liquid component.

14. The method of claim 1 further comprising concentrating the particulate component in a central zone of the flow channel, wherein the particulate component comprises blood cells.

15. The method of claim 1 further comprising expanding a width of the flow channel, at a collection zone to maintain laminar flow and to avoid turbulence.

16. The method of claim 1 further comprising performing in vitro diagnostic analysis using the liquid component, wherein the liquid component comprises at least one of blood plasma or blood serum.

17. The method of claim 1 further comprising aligning the particulate component along one or more light paths using flow cytometry, wherein the particulate component comprises cells.

18. The method of claim 1, wherein the sample of fluid is whole blood, the particulate component comprises blood cells, and the liquid component comprises at least one of blood plasma or blood serum.

19. The method of claim 1, wherein introducing the sample of fluid comprises introducing the sample of fluid into an inlet port of the inlet channel.

20. The method of claim 1, wherein collecting the liquid component comprises removing the liquid component via the first outlet channel and an outlet port of the first outlet channel.

21. The method of claim 1 further comprising collecting the particulate component.

22. The method of claim 21, wherein the particulate component is collected at a first location and the liquid component is collected at a second location different than the first location.

23. The method of claim 22 further comprising adjusting one or more of a width of the flow channel or a wavelength of at least one of the transducers to change at least one of the first location or the second location.

24. The method of claim 1, wherein each of the transducers has triangular cross-sectional area.

25. The method of claim 1 further comprising introducing a buffer into the flow channel.

26. The method of claim 25, wherein the buffer comprises phosphate buffered saline.

27. The method of claim 1 further comprising adjusting a wavelength of one or more of the transducers based on a width of the flow channel.

28. The method of claim 27, wherein the width is one half the wavelength.

29. The method of claim 1, wherein the apparatus further comprises a third outlet channel coupled to the second section.

30. The method of claim 29, wherein the first outlet channel is positioned opposite the flow channel from the third outlet channel.

31. The method of claim 29, wherein collecting the liquid component comprises removing the liquid component via the first outlet channel and the third outlet channel.

32. The method of claim 31 further comprising collecting the particulate component via the second outlet channel.

33. The method of claim 1, the second outlet to collect the particulate component.

34. The method of claim 1, wherein the laminar flow causes the particulate component to flow in a forward direction through the first, second and third sections of the flow channel.

35. A method comprising:
providing an acoustic field within a flow channel, the field comprising acoustic standing waves;
maintaining a laminar flow of a sample of fluid in the flow channel, the flow channel defined by a first side wall and a second side wall opposite the first side wall, the sample comprising a particulate component suspended in a liquid component;
separating the particulate component from the liquid component using an outlet port that extends through the first sidewall and into the flow channel, a portion of the outlet port axially aligned with the flow channel; and
collecting the liquid component.

* * * * *